United States Patent
Wei et al.

(10) Patent No.: US 10,799,127 B2
(45) Date of Patent: Oct. 13, 2020

(54) SYSTEM AND METHOD FOR PHYSIOLOGICAL PARAMETER MONITORING

(71) Applicant: VITA-COURSE TECHNOLOGIES CO., LTD., Shenzhen, Guangdong (CN)

(72) Inventors: Chuanmin Wei, Shenzhen (CN); Ting Ma, Shenzhen (CN); Jiao Yu, Shenzhen (CN); Zhiyong Wang, Shenzhen (CN); Jiwei Zhao, Shenzhen (CN)

(73) Assignee: VITA-COURSE TECHNOLOGIES CO., LTD., Shenzhen (CN)

( * ) Notice: Subject to any disclaimer, the term of this patent is extended or adjusted under 35 U.S.C. 154(b) by 321 days.

(21) Appl. No.: 15/563,569

(22) PCT Filed: Dec. 5, 2015

(86) PCT No.: PCT/CN2015/096498
§ 371 (c)(1),
(2) Date: Sep. 30, 2017

(87) PCT Pub. No.: WO2016/155348
PCT Pub. Date: Oct. 6, 2016

(65) Prior Publication Data
US 2018/0085012 A1    Mar. 29, 2018

Related U.S. Application Data

(63) Continuation of application No. PCT/CN2015/083334, filed on Jul. 3, 2015.

(30) Foreign Application Priority Data

Mar. 31, 2015  (CN) .................... 2015 2 0188152 U

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/0225* (2013.01); *A61B 5/0245* (2013.01);
(Continued)

(58) Field of Classification Search
CPC .......... A61B 2560/0228; A61B 5/0205; A61B 5/021; A61B 5/02125; A61B 5/02255;
(Continued)

(56) References Cited

U.S. PATENT DOCUMENTS

| 5,626,135 A | 5/1997 | Sanfilippo |
| 5,873,834 A | 2/1999 | Yanagi et al. |

(Continued)

FOREIGN PATENT DOCUMENTS

| CN | 1698535 A | 11/2005 |
| CN | 101327121 A | 12/2008 |

(Continued)

OTHER PUBLICATIONS

Emil F. Pascarelli et al., Comparison of Blood Pressures in the Arms and Legs, The New England Journal of Medicine, 270(14): 693-698, 1964.

(Continued)

*Primary Examiner* — Christine H Matthews
(74) *Attorney, Agent, or Firm* — Metis IP LLC

(57) ABSTRACT

A device, method and system for calculating, estimating, or monitoring the blood pressure of a subject. A first signal representing heart activity of a subject may be received. A plurality of second signals representing time-varying information on at least one pulse wave of the subject may be received from a plurality of body locations of the subject. A first feature of the first signal may be identified. For each of the plurality of second signals, a second feature may be identified. A pulse transit time based on a difference of the first feature and at least one of the second features may be (Continued)

computed. A blood pressure of the subject may be calculated according to a model based on the computed pulse transit time. The model may include a compensation term relating to the plurality of second signals or the second features thereof.

20 Claims, 15 Drawing Sheets

(51) Int. Cl.
*A61B 5/021* (2006.01)
*A61B 5/0225* (2006.01)
*A61B 5/0245* (2006.01)
*A61B 5/11* (2006.01)
*A61B 5/145* (2006.01)
*A61B 5/1455* (2006.01)
*G06F 21/31* (2013.01)
*A61B 5/026* (2006.01)
*A61B 5/0205* (2006.01)
*A61B 5/01* (2006.01)
*A61B 5/0456* (2006.01)

(52) U.S. Cl.
CPC ...... *A61B 5/02125* (2013.01); *A61B 5/02255* (2013.01); *A61B 5/1102* (2013.01); *A61B 5/14542* (2013.01); *A61B 5/14551* (2013.01); *A61B 5/7203* (2013.01); *A61B 5/7235* (2013.01); *A61B 5/746* (2013.01); *G06F 21/31* (2013.01); *A61B 5/01* (2013.01); *A61B 5/021* (2013.01); *A61B 5/0205* (2013.01); *A61B 5/026* (2013.01); *A61B 5/0456* (2013.01); *A61B 2560/0228* (2013.01)

(58) Field of Classification Search
CPC ... A61B 5/02416; A61B 5/0245; A61B 5/026; A61B 5/7235
See application file for complete search history.

(56) References Cited

U.S. PATENT DOCUMENTS

| | | | |
|---|---|---|---|
| 6,355,000 | B1 | 3/2002 | Ogura |
| 6,533,729 | B1 | 3/2003 | Khair et al. |
| 7,887,491 | B2 | 2/2011 | Marks et al. |
| 8,602,997 | B2 | 12/2013 | Banet et al. |
| 9,439,599 | B2 | 9/2016 | Thompson et al. |
| 9,865,176 | B2 | 1/2018 | Tran |
| 2003/0167012 | A1 | 9/2003 | Friedman et al. |
| 2005/0208969 | A1 | 9/2005 | Kwoen |
| 2007/0100247 | A1 | 5/2007 | Platt et al. |
| 2008/0039731 | A1 | 2/2008 | McCombie et al. |
| 2008/0221461 | A1 | 9/2008 | Zhou et al. |
| 2009/0105605 | A1 | 4/2009 | Abreu |
| 2010/0049006 | A1 | 2/2010 | Magar et al. |
| 2011/0009718 | A1 | 1/2011 | Gavish |
| 2011/0066045 | A1 | 3/2011 | Moon et al. |
| 2012/0101350 | A1 | 4/2012 | Bychkov |
| 2012/0136261 | A1 | 5/2012 | Sethi et al. |
| 2012/0316448 | A1 | 12/2012 | Gu et al. |
| 2013/0012823 | A1 | 1/2013 | Ripoll et al. |
| 2013/0053655 | A1 | 2/2013 | Castellanos |
| 2013/0197369 | A1 | 8/2013 | Xiang |
| 2014/0066788 | A1 | 3/2014 | Mukkamala et al. |
| 2014/0206976 | A1 | 7/2014 | Thompson et al. |
| 2015/0018637 | A1 | 1/2015 | Chen et al. |
| 2015/0125832 | A1 | 5/2015 | Tran |
| 2015/0320359 | A1 | 11/2015 | Luo |
| 2017/0109495 | A1 | 4/2017 | Xin |
| 2018/0116597 | A1 | 5/2018 | Yu et al. |
| 2018/0132744 | A1 | 5/2018 | Yu et al. |
| 2018/0160905 | A1 | 6/2018 | Wang et al. |

FOREIGN PATENT DOCUMENTS

| | | | |
|---|---|---|---|
| CN | 101732040 | A | 6/2010 |
| CN | 101810470 | A | 8/2010 |
| CN | 102008296 | A | 4/2011 |
| CN | 102397064 | A | 4/2012 |
| CN | 102429649 | A | 5/2012 |
| CN | 102438503 | A | 5/2012 |
| CN | 202505340 | U | 10/2012 |
| CN | 103190891 | A | 7/2013 |
| CN | 103385702 | A | 11/2013 |
| CN | 103598876 | A | 2/2014 |
| CN | 103637787 | A | 3/2014 |
| CN | 204044771 | U | 12/2014 |
| CN | 104257371 | A | 1/2015 |
| CN | 104323764 | A | 2/2015 |
| CN | 104382571 | A | 3/2015 |
| CN | 104706348 | A | 3/2015 |
| CN | 204207743 | U | 3/2015 |
| CN | 104523252 | A | 4/2015 |
| CN | 104665768 | A | 6/2015 |
| CN | 104720773 | A | 6/2015 |
| CN | 204499693 | U | 7/2015 |
| CN | 204506976 | U | 7/2015 |
| CN | 204674751 | U | 9/2015 |
| WO | 2012040931 | A1 | 4/2012 |
| WO | 2014195578 | A1 | 12/2014 |
| WO | 2016155138 | A1 | 10/2016 |
| WO | 2017005016 | A1 | 1/2017 |

OTHER PUBLICATIONS

A. G. Hocken et al., Measurement of Blood-Pressure in the Leg, The Lancet, 466-468, 1967.

Helios De Rosario et al., Using Smart Materials to Monitor Physiological Signals of Driver's Inattention.

Matteo Stoppa et al., Wearable Electronics and Smart Textiles: A Critical Review, Sensors 2014, 14: 11957-11992, 2014.

Li Li et al., A Study on Comparing Blood Pressure of Ankle Artery with Brachial Artery and Intra-aortic Pressures, Chinese Journal of Cardiology, 27(5), 1999.

Wang Chunxiang et al., Analysis of Blood Pressure Measurements from the Brachial and Radial Arteries in Children, Chinese Journal of Nursing, 36(3): 171-172, 2001.

Xu Peng et al., On Different Operative Methods for Hypertensive Intracerebral Hemorrhage at Different Locations, Chinese Journal of Minimally Invasive Surgery, 4(5): 430-431, 2004.

Du Lixia et al., Correlation and Clinical Significance of Blood Pressure in Different Parts of Elderly Patients with Cardiovascular Disease, Xinjiang Journal of Traditional Chinede Medicine, 25(5): 21-23, 2007.

Peng Jubao et al., The Nature and Clinical Significance of the Difference in Blood Pressure Measurement of Limbs, Medicine and Philosophy, 3: 39-40,1987.

Hu Gijoxun et al., Comparative Study on Blood Pressure Measurement Methods of Lower Limbs, Shanxi Medicine Joural, 34(4): 333-334, 2005.

Wang Pengju et al., Mechanical Relation between Cuff and Limb with Special Reference to Its Effects on Accuracy of Blood Pressure Measurement, Chinese Journal of Physical Medicine, 16(3): 175-178, 1994.

Hou Guizhi et al., Estimation of Brachial Artery Blood Pressure from Radial Artery Blood Pressure, Journal of Practical Nursing, 8(5): 5-6, 1992.

International Search Report in PCT/CN2016/077469 dated Jun. 8, 2016, 5 pages.

Written Opinion in PCT/CN2016/077469 dated Jun. 8, 2016, 4 pages.

International Search Report in PCT/CN2017/076702 dated Jun. 7, 2017, 5 pages.

Written Opinion in PCT/CN2017/076702 dated Jun. 7, 2017, 5 pages.

International Search Report in PCT/CN2015/083334 dated Dec. 18, 2015, 7 pages.

(56) References Cited

OTHER PUBLICATIONS

Written Opinion in PCT/CN2015/083334 dated Dec. 18, 2015, 6 pages.
International Search Report in PCT/CN2016/070017 dated Apr. 13, 2016, 6 pages.
Written Opinion in PCT/CN2016/070017 dated Apr. 13, 2016, 8 pages.
Extended European Search Report in European Application No. 17773043.9 dated Mar. 21 2019, 6 pages.
Ji Won Lee et al., Noise Reduction and Adaptive Contrast Enhancement for Local Tone Mapping, IEEE Transactions on Consumer Electronics, 58(2): 578-586, 2012.
International Search Report in International Application No. PCT/CN2015/096498 dated Mar. 9, 2016, 7 pages.
Writtern Opinion in International Application No. PCT/CN2015/096498 dated Mar. 9, 2016, 5 pages.
Extended European Search Report in European Application No. 17773043.9 dated Mar. 21, 2019, 8 pages.
The Second Office Action in Chinese Application No. 201580078735.9 dated Mar. 16, 2020, 25 pages.

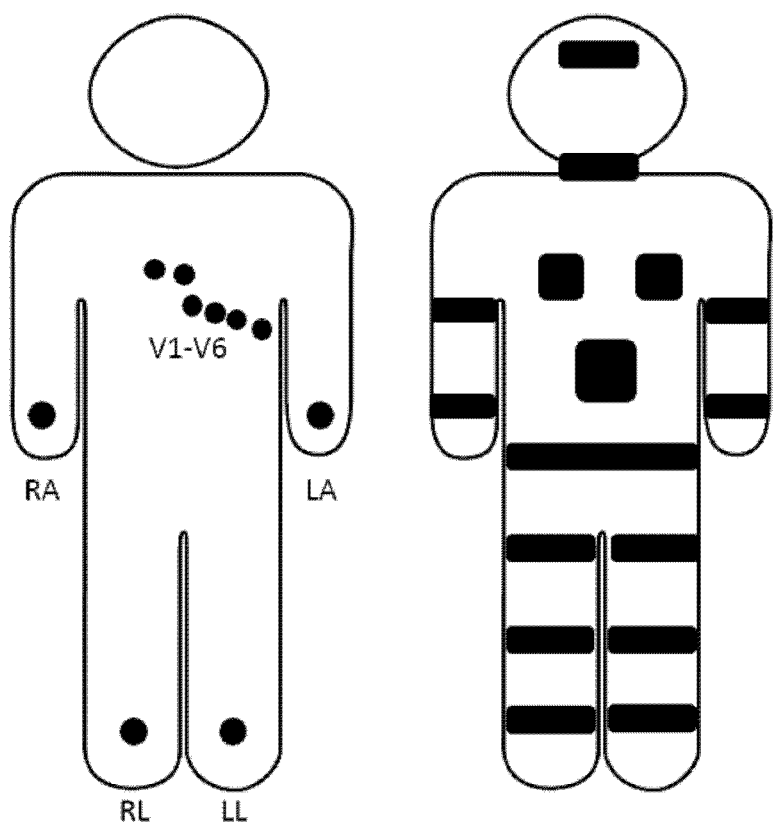
FIG. 5-A                    FIG. 5-B

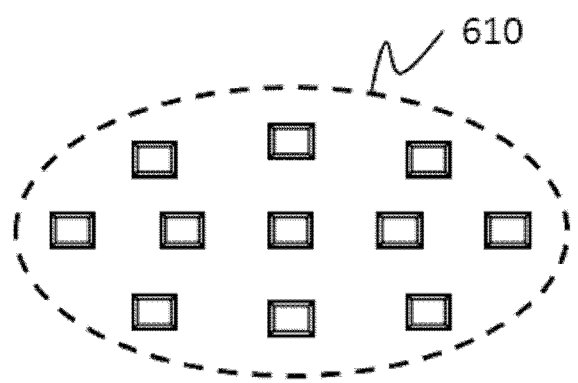
FIG. 6-A
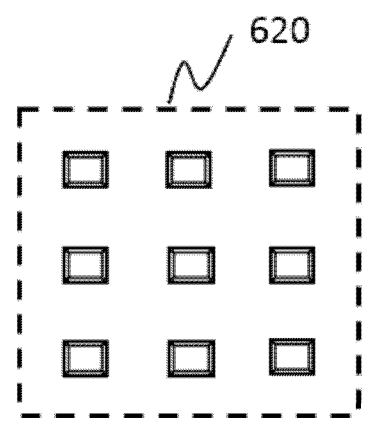
FIG. 6-B
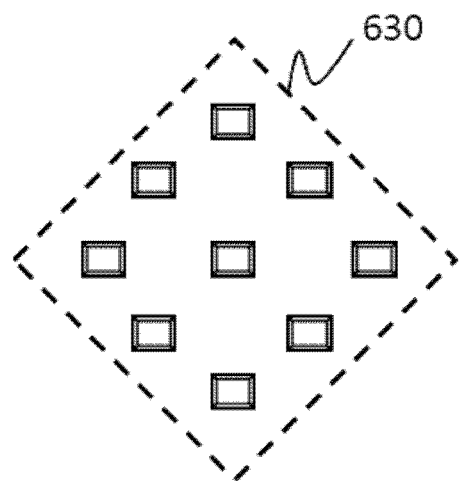
FIG. 6-C
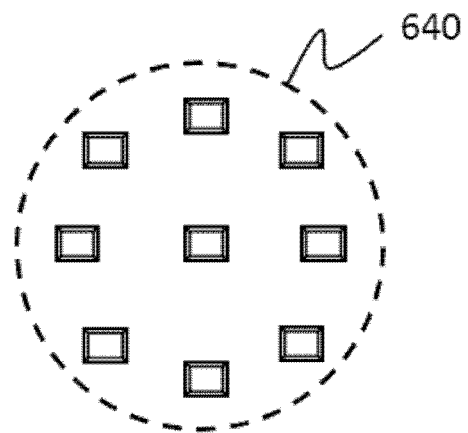
FIG. 6-D

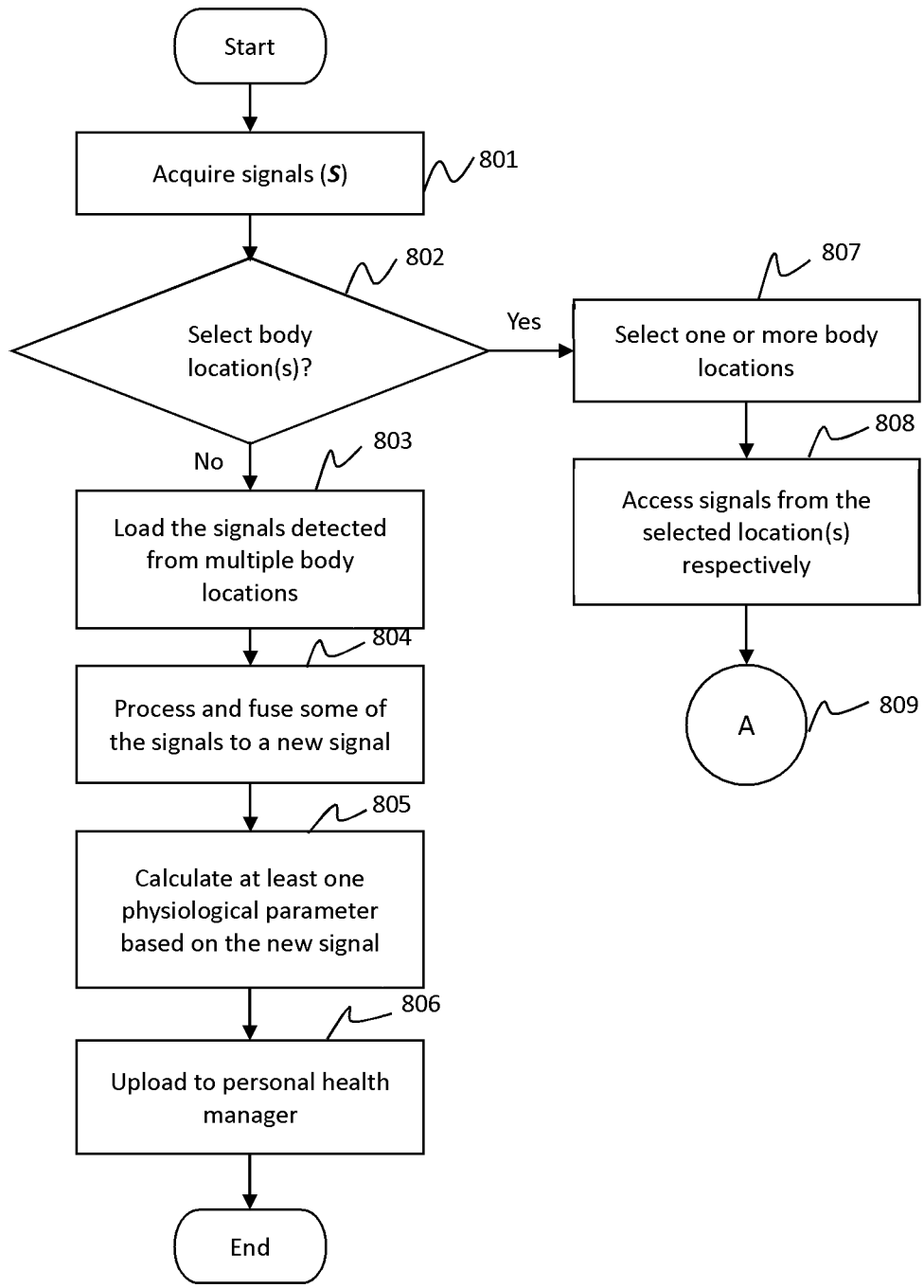
FIG. 8-A

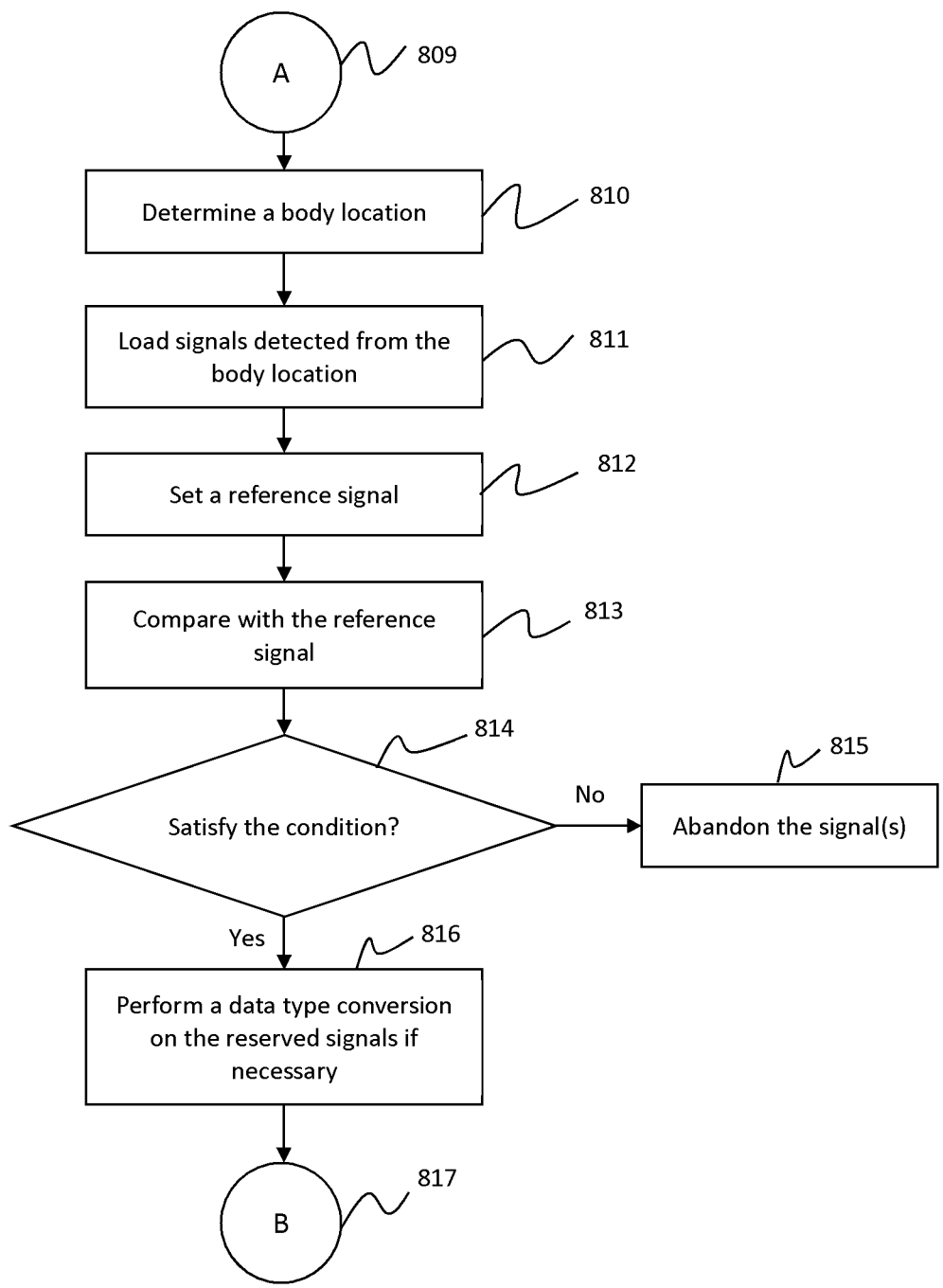
FIG. 8-B

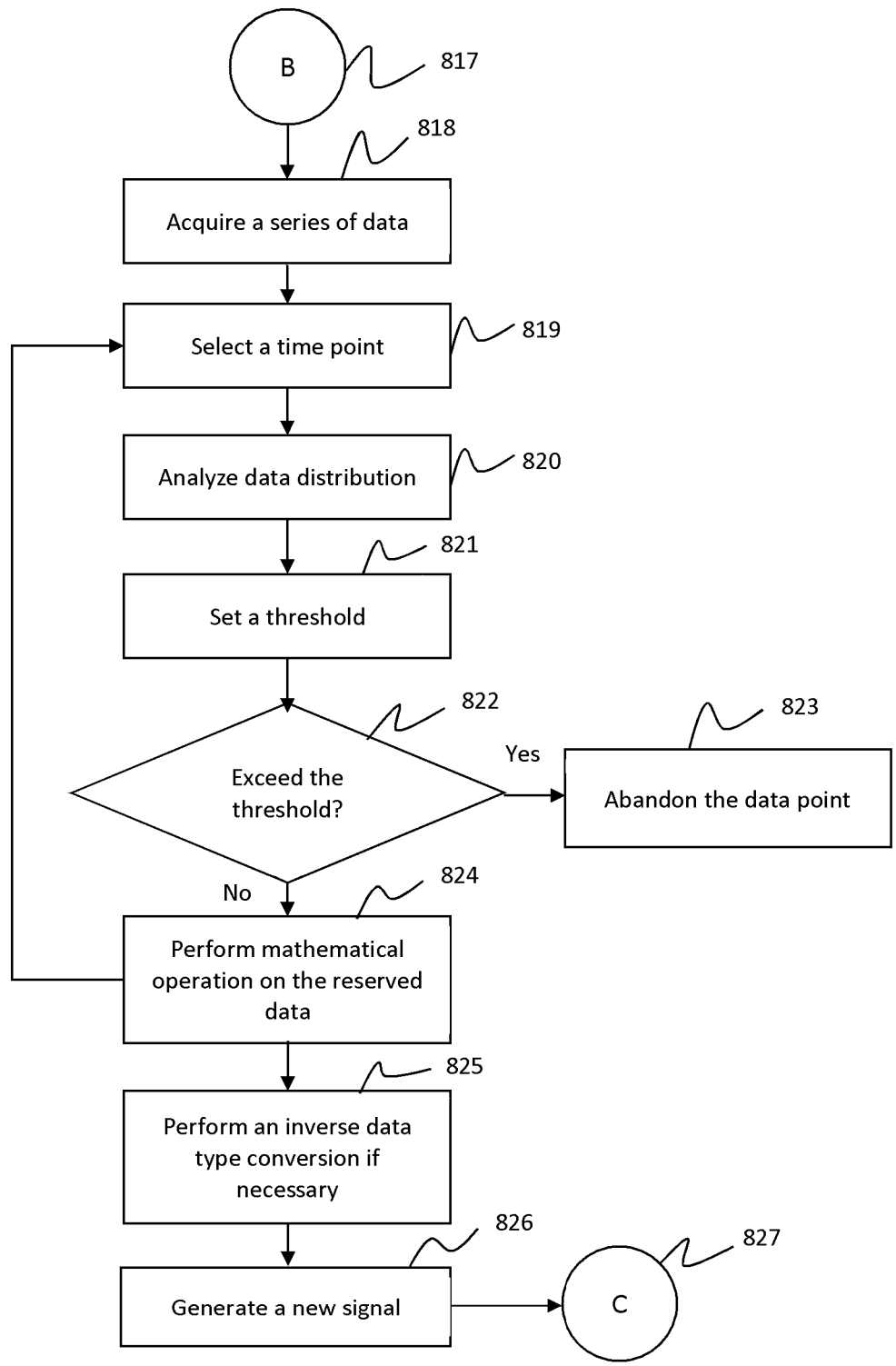
FIG. 8-C

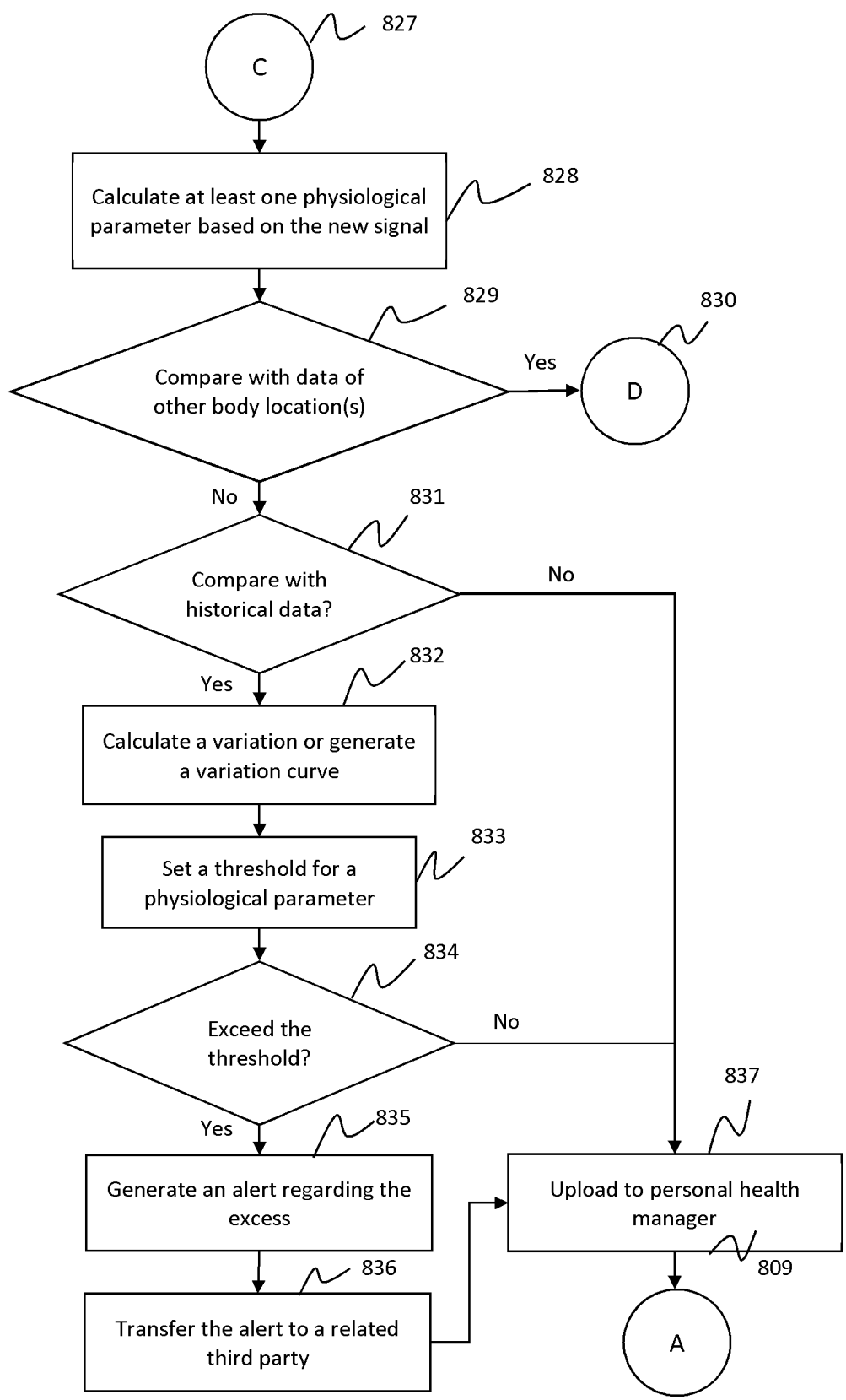
FIG. 8-D

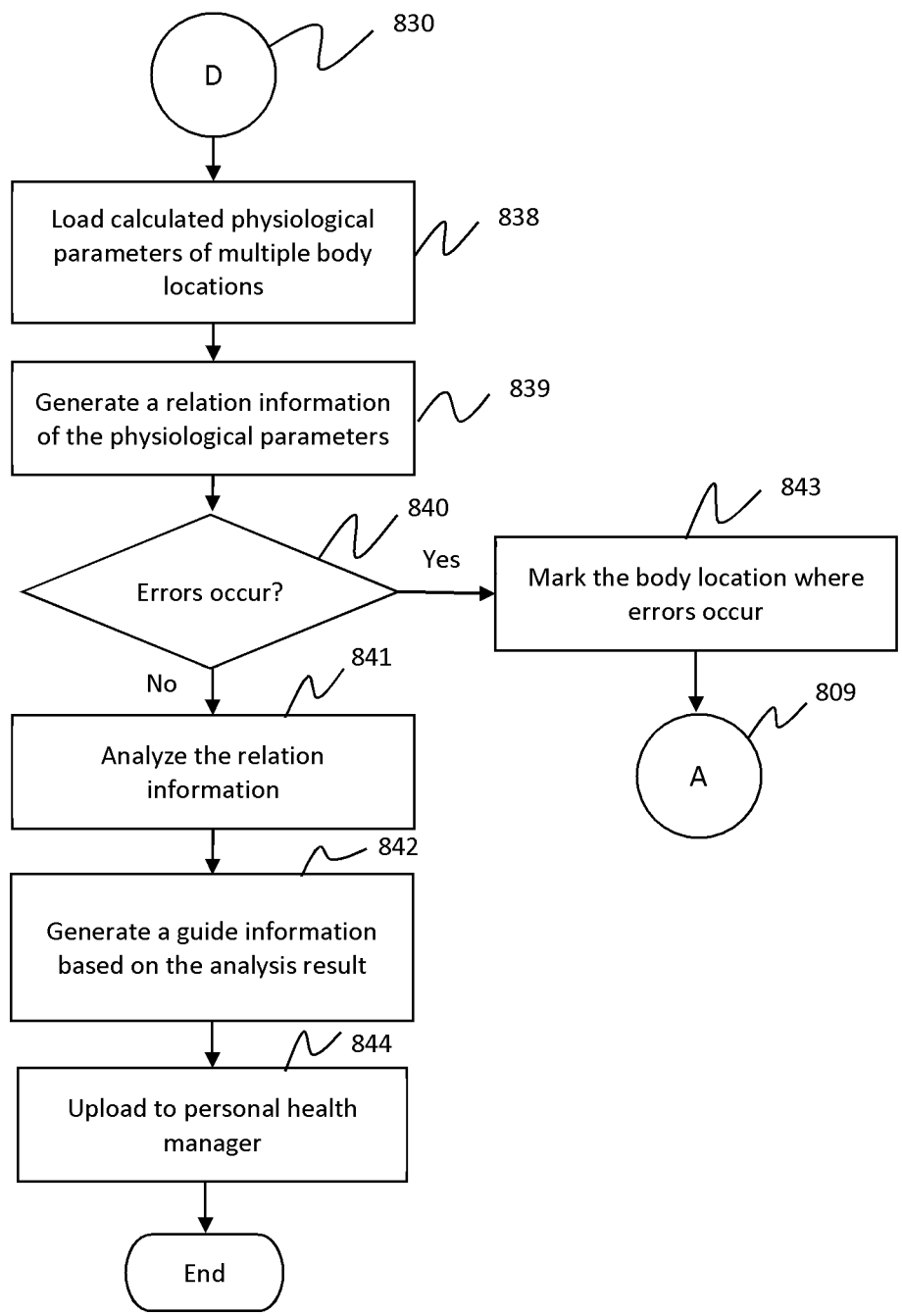
FIG. 8-E

SYSTEM AND METHOD FOR PHYSIOLOGICAL PARAMETER MONITORING

CROSS-REFERENCE TO RELATED APPLICATIONS

This application is a U.S. national phase entry of International Application No. PCT/CN2015/096498, filed on Dec. 5, 2015, which claims priority to International Application No. PCT/CN2015/083334 filed Jul. 3, 2015, which claims priority to Chinese Patent Application No. 201520188152.9 filed Mar. 31, 2015. Each of the above-referenced applications is incorporated herein by reference to their entireties.

TECHNICAL FIELD

The present disclosure generally relates to a system and method applicable in health-care related areas. More particularly, the present disclosure relates to a system and method for blood pressure monitoring.

BACKGROUND

A traditional blood pressure measurement system, also called sphygmomanometers, employs Korotkoff sounds or an oscillometric method to determine blood pressure based on the relationship of the external pressure and magnitude of arterial volume pulsations. Such a traditional blood pressure measurement system involves an inflatable cuff to restrict blood flow. Various cuff-based methods work discontinuously with an interval of some minutes or longer between consecutive measurements. Currently, ambulatory blood pressure measurement and home blood pressure measurement are recommended by professional societies for hypertension management and cardiovascular risk prediction. However, such intermittent blood pressure measurements cannot capture the dynamic state of cardiovascular system throughout a day or even longer time period. Continuous and non-invasive blood pressure monitoring may allow the investigation of transient changes in blood pressure and thus may give insights into mechanisms of blood pressure control. There is a need for a system and method to monitor blood pressure continuously in a non-invasive and cuffless way with certain accuracy.

SUMMARY

Some embodiments of the present disclosure relates to a device including memory storing instructions, and at least one processor. The device may be used to calculate, estimate, or monitor the blood pressure of a subject. When the at least one processor executing the instructions, the at least one processor may perform one or more of the following operations. A first signal representing heart activity the subject, or first information relating to or representing the first signal, may be received. A plurality of second signals representing time-varying information on at least one pulse wave of the subject, or second information relating to or representing the second signal, may be received. The second signals or the second information may be from a plurality of body locations of the subject (or referred to as locations of the body of the subject, or locations of the subject). A first feature of the first signal may be identified. The identification of the first feature in the first signal may be achieved by analyzing the first information or the first signal. For each of the plurality of second signals, a second feature may be identified. The identification of the second feature of one of the plurality of second signals may be achieved by analyzing the second information or the second signal. A pulse transit time based on a difference of the first feature and at least one of the second features may be computed. In some embodiments, a blood pressure of the subject may be calculated according to a model based on the computed pulse transit time. The model may include a compensation term relating to the plurality of second signals or the second features thereof.

Some embodiments of the present disclosure relates to a method implemented on at least one processor for calculating, estimating, or monitoring the blood pressure of a subject. The method may include one or more of the following operations. A first signal representing heart activity the subject, or first information relating to or representing the first signal, may be received. A plurality of second signals representing time-varying information on at least one pulse wave of the subject, or second information relating to or representing the second signal, may be received. The second signals or the second information may be from a plurality of body locations of the subject (or referred to as locations of the body of the subject, or locations of the subject). A first feature of the first signal may be identified. The identification of the first feature in the first signal may be achieved by analyzing the first information or the first signal. For each of the plurality of second signals, a second feature may be identified. The identification of the second feature of one of the plurality of second signals may be achieved by analyzing the second information or the second signals. A pulse transit time based on a difference of the first feature and at least one of the second feature may be computed. In some embodiments, a blood pressure of the subject may be calculated according to a model based on the computed pulse transit time. The model may include a compensation term relating to the plurality of second signals or the second features thereof.

Some embodiments of the present disclosure relates to a system implemented on memory and at least one processor. The system may be used to calculate, estimate, or monitoring the blood pressure of a subject. The system may include an acquisition module and an analysis module. The acquisition module may be configured to receive a first signal representing heart activity of a subject (or first information relating to or representing the first signal), and a plurality of second signals representing time-varying information on at least one pulse wave of the subject (or second information relating to or representing the second signal). The second signals or the second information may be from a plurality of body locations of the subject (or referred to as locations of the body of the subject, or locations of the subject). The analysis module may be configured to identify a first feature in the first signal; identify, for each of the plurality of second signals, a second feature; compute a pulse transit time based on a difference between the first feature and one of the second features; and calculate a blood pressure of the subject according to a model based on the computed pulse transit time. The model may include a compensation term relating to the plurality of second signals or the second features thereof. The identification of the first feature in the first signal may be achieved by analyzing the first information or the first signal. The identification of the second feature in the plurality of second signals may be achieved by analyzing the second information or the second signals. The system may further include an output module configured to provide the calculated blood pressure for output.

In some embodiments, a plurality of pulse transit time values may be computed. The value of pulse transit time may be computed based on the difference between the first feature of a first signal and the second feature of a second signal. The second signals may be from different locations of the body of a same subject. The plurality of pulse transit time values may be based on a same first signal or different first signals. For instance, two pulse transit time values may be based on one first signal and two second signals from two locations of the body of the subject. As another example, two pulse transit time values may be based on two different first signals and two second signals from two locations of the body of the subject. As used herein, different signals may be acquired from the same location of the body of a subject at different times, or acquired from different locations of the body of a subject approximately the same time or at different times. For instance, different first signals or different second signals may be acquired from the same location of the body of the subject at different times. As another example, different first signals or different second signals may be acquired from different locations of the body of a subject approximately the same time or at different times. In some embodiments, a plurality of blood pressure values of the subject may be calculated according to a model based on the computed pulse transit time values. In some embodiments, a plurality of blood pressure values of the subject may be calculated according to multiple models based on the computed pulse transit time values. Such models may be selected based on the location(s) where the first signal or the second signal whose feature(s) is/are used to compute the pulse transit time have been acquired. For instance, second signals are acquired from an upper arm and at an ankle of the subject, the second features of these two second signals are identified, and two pulse transit time values are computed based on the two second features and a first feature of a same first signal; two blood pressure values may be calculated based on the two pulse transit time values according to a same model, or according to two different models; the two models may be selected based on the locations (the upper arm and the ankle) where the two second signals have been acquired.

In some embodiments, receiving the first signal may include communicating with a first sensor configured to acquire the first signal at a first location on the body of the subject. Receiving the first signal may include measuring or acquiring the first signal using a first sensor configured to acquire the first signal at a first location on the body of the subject. The first sensor may be part of the device. In some embodiments, the receiving the plurality of second signals may include communicating with a plurality of second sensors configured to acquire the plurality of second signals at a plurality of second locations on the body of the subject. In some embodiments, the receiving the plurality of second signals may include communicating with a plurality of second sensor arrays configured to acquire the plurality of second signals at a plurality of second locations on the body of the subject. The second sensors or the second sensor arrays may be a part of the device. The first location and one of the second locations may be substantially the same. The second locations may include head, the neck, the chest, the abdomen, the upper arm, the wrist, the waist, the upper leg, the knee, or the ankle of the subject. The device may include a structure that allows the device to be worn by the subject.

In some embodiments, at least one of the plurality of second sensor arrays may include a plurality of sensors, a plurality of receiving ends of a one or more sensors, or a plurality of emitting ends of one or more sensors. In some embodiments, the configuration of the sensor array may be an oval array, a rectangular array, a circular array or a triangular array.

In some embodiments, the first signal may include an optical signal or an electrical signal. The second signal may include an optical signal or an electrical signal. The first signal or the second signal may include a photoplethysmography (PPG) waveform, an electrocardiography (ECG) waveform, or a ballistocardiogram (BCG) waveform.

In some embodiments, a plurality of blood pressures of the plurality of second locations may be calculated. In some embodiments, relation information may be generated. For example, the relation information may include a distribution of blood pressure values of a plurality of body locations (for example, the left ankle versus the right ankle, the left upper arm versus the right upper arm) of the subject. As another example, the relation information may include a comparison of the blood pressure value at a body location with a reference value. Exemplary reference values may include one or more historic blood pressure values at the same or similar location of the subject, of a sub-group of people who share a same or similar characteristic with the subject, or a general population. In some embodiments, the pulse transit time values on the basis of which the blood pressure values are calculated may be used, instead of the blood pressure values themselves, to generate the relation information. In some embodiments, a recommendation relating to the subject may be provided based on the relation information. In some embodiments, the recommendation may include a compensation term regarding the model to be used to calculate blood pressure. In some embodiments, the recommendation may be a prompting message regarding selection of a model that may be used to calculate blood pressure. In some embodiments, the recommendation may include a model that may be used to calculate blood pressure. The model may include the modified first model by the compensation term. In some embodiments, the recommendation may be a push information regarding daily activities of the subject.

In some embodiments, the at least one processor may further receive information relating to the subject or a condition when the first signal or the second signal is acquired. Exemplary information may include, e.g., age, body weight, the time (during the day) or the date the first signal or the second signal is acquired, the room temperature, the mood of the subject at the time, whether the subject has recently exercised, or the like, or a combination thereof. Such information may be taken into consideration when the blood pressure of the subject is calculated using the device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5-A and FIG. 5-B are schematic diagrams showing the arrangement or the location of the ECG sensors and PPG sensors according to some embodiments of the present disclosure;

FIG. 6-A through FIG. 6-D are schematic diagrams showing exemplary sensor arrays of PPG sensors according to some embodiments of the present disclosure;

FIG. 8-A through FIG. 8-E provide exemplary signal processing according to some embodiments of the present disclosure;

DETAILED DESCRIPTION

Figure 1:
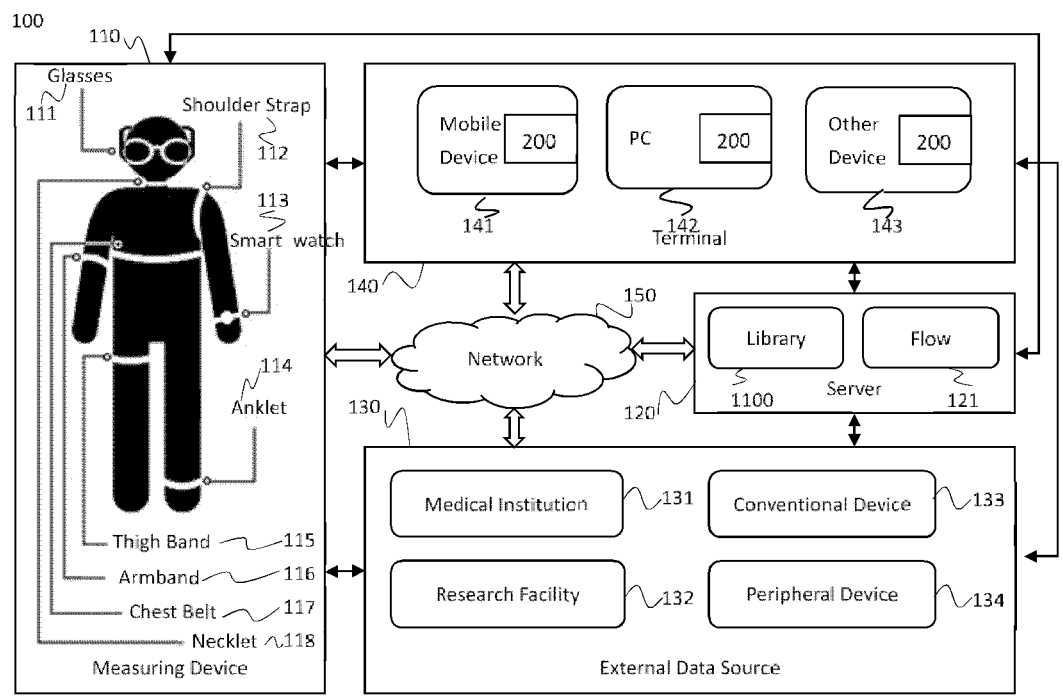
FIG. 1 illustrates an exemplary system configuration in which a system for monitoring a physiological signal may be deployed in accordance with various embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure.

The present disclosure relates to system, method, and programming aspects of blood pressure monitoring. The blood pressure monitoring may involve a cuffless system and method. In some embodiments, blood pressure is estimated based on pulse wave related information, for example, pulse transit time (PTT), pulse arrival time (PAT), or the like, or a combination thereof. The system and method involve improved sensor design and signal processing. The system and method as disclosed herein may perform blood pressure monitoring continuously in a non-invasive way, with improved accuracy. The system and method as disclosed herein may perform blood pressure monitoring of multiple body locations in real time. The following description is provided with reference to PTT in connection with the blood pressure monitoring for illustration purposes, and is not intended to limit the scope of the present disclosure. Merely by way of example, the system and method as disclosed herein may utilize one or more other pulse wave related information or signals, for example, PAT, for blood pressure monitoring.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purposes of illustration and description only and are not intended to limit the scope of the present disclosure. As used in the specification and in the claims, the singular form of "a," "an," and "the" include plural referents unless the context clearly dictates otherwise.

FIG. 1 illustrates an exemplary system configuration in which a system 100 may be deployed in accordance with some embodiments of the present disclosure. The system 100 may be configured to monitor a physiological parameter of interest. The system 100 may include a measuring device 110, a database (for example, a server 120), an external data source 130, and a terminal 140. Various components of the system 100 may be connected to each other directly or indirectly via a network 150.

The measuring device 110 may be configured to measure a signal. The signal may be a cardiovascular signal. The signal may relate to or be used to calculate or estimate a physiological parameter of interest. The measuring device 110 may include, for example, a clinical device, a household device, a portable device, a wearable device, or the like, or a combination thereof. As used herein, a clinical device may be one that meets applicable standards and/or specifications to be used in a clinical setting including, for example, a hospital, a doctor's office, a nursing home, or the like. A clinical device may be used by or with the assistance of a healthcare provider. As used herein, a household device may be one that meets applicable standards and/or specifications to be used at home or a nonclinical setting. A household device may be used by someone who is or is not a professional provider. A clinical device or a household device, or a portion thereof, may be portable or wearable. Exemplary clinical devices include an auscultatory device, an oscillometric device, an ECG monitor, a PPG monitor, or the like, or a combination thereof. Exemplary household devices include an oscillometric device, a household ECG monitor, a sphygmometer, or the like, or a combination thereof. Exemplary portal devices include an oscillometric device, a portable ECG monitor, a portable PPG monitor, or the like, or a combination thereof. Exemplary wearable devices include a pair of glasses 111, a shoulder strap 112, a smart watch 113, an anklet 114, a thigh band 115, an armband 116, a chest belt 117, a necklet 118, or the like, or a combination thereof. The above mentioned examples of measuring devices 110 are provided for illustration purposes, and not intended to limit the scope of the present disclosure. A measuring device 110 may be in another form including, for example, a fingerstall, a wristband, a brassiere, an underwear, a chest band, or the like, or a combination thereof.

Merely by way of example, the measuring device 110 is a wearable or portable device configured to measure one or more cardiovascular signals. In some embodiments, the wearable or portable device may process at least some of the measured signals, estimate a physiological parameter of interest based on the measured signals, display a result including the physiological parameter of interest in the form of, for example, an image, an audio alert, perform wired or wireless communication with another device or server (for example, the server 120), or the like, or a combination thereof. In some embodiments, the wearable or portable device may communicate with another device (for example, the terminal 140) or a server (for example, a cloud server). The device or server may process at least some of the measured signals, estimate a physiological parameter of interest based on the measured signals, display a result including the physiological parameter of interest in the form of, for example, an image, an audio alert, or the like, or a combination thereof.

In some embodiments, the operations of processing the measured signals, estimating a physiological parameter, displaying a result, or performing wired or wireless communication may be performed by an integrated device or by separate devices connected to or communicating with each other. Such an integrated device may be portable or wearable. In some embodiments, at least some of the separate devices may be portable or wearable, or located in the vicinity of a subject whose signal is measured or a physiological parameter of interest is estimated or monitored. Merely by way of example, the subject wears the measuring device 110 that is configured to measure one or more cardiovascular signals; the measured one or more cardiovascular signals are transmitted to a smart phone that is configured to calculate or estimate a physiological parameter of interest based on the measured signals. In some embodiments, at least some of the separate devices are located in a location remote from the subject. Merely by way of example, the subject wears the measuring device 110 that is configured to measure one or more cardiovascular signals; the measured one or more cardiovascular signals are transmitted to a server that is configured to calculate or estimate a physiological parameter of interest based on the measured signals; the calculated or estimated physiological parameter of interest may be transmitted back to the subject, or a user other than the subject (for example, a doctor, a care provider, a family member relating to the subject, or the like, or a combination thereof).

In some embodiments, the measuring devices 110 may incorporate various types of sensors including, for example, an electrode sensor, an optical sensor, a photoelectric sensor, a pressure sensor, an accelerometer, a gravity sensor, a temperature sensor, a moisture sensor, or the like, or a combination thereof. The measuring device may be configured to monitor and/or detect one or more types of variables including, for example, temperature, humidity, user or subject input, or the like, or a combination thereof. The measuring devices 110 may also incorporate a positioning system, for example, a GPS receiver, or a location sensor, and the position information may be transmitted to the server 120, the external data source 130, the terminal 140, or the like, or a combination thereof, through the network 150. The position information and measured signals may be transmitted simultaneously or successively.

The system may include or communicate with a server or a database configured for storing a library 1100 and/or algorithms 121. The server or database may be the server 120. The server 120 may be a cloud server. Merely by way of example, the server 120 may be implemented in a cloud server that may provide storage capacity, computation capacity, or the like, or a combination thereof. The library 1100 may be configured to collect or store data. The data may include personal data, non-personal data, or both. The data may include static data, dynamic data, or both. Exemplary static data may include various information regarding a subject including identity, contact information, birthday, a health history (for example, whether a subject has a history of smoking, information regarding a prior surgery, a food allergy, a drug allergy, a medical treatment history, a history of genetic disease, a family health history, or the like, or a combination thereof), the gender, the nationality, the height, the weight, the occupation, a habit (for example, a health-related habit such as an exercise habit), the education background, a hobby, the marital status, religious belief, or the like, or a combination thereof. Exemplary dynamic data may include a current health condition of a subject, medications the subject is taking, a medical treatment the subject is undertaking, diet, physiological signals or parameters (for example, pulse transit time (PTT), systolic blood pressure (SBP), diastolic blood pressure (DBP), or the like) relating to the subject for multiple time points or over a period of time, or the like, or a combination thereof.

As used herein, a subject may refer to a person or animal whose signal or information is acquired and whose physiological parameter is acquired, estimated, or monitored. Merely by way of example, a subject may be a patient whose cardiovascular signals are acquired, and blood pressure estimated or monitored based on the acquired cardiovascular signals.

One or more algorithms 121 in the server 120 may be applied in data processing or analysis, as described elsewhere in the present disclosure. The description of the server 120 above is provided for illustration purposes, and not intended to limit the scope of the present disclosure. The server 120 may have a different structure or configuration. For example, algorithms 121 are not stored in the server 120; instead, the algorithms 121 may be stored locally at the terminal 140. Furthermore, a library 1100 may also be stored at the terminal 140.

The external data sources 130 may include a variety of organizations, systems, and devices, or the like, or a combination thereof. Exemplary data sources 130 may include a medical institution 131, a research facility 132, a conventional device 133, and a peripheral device 134, or the like, or a combination thereof. The medical institution 131 or the research facility 132 may provide, for example, personal medical records, clinical test results, experimental research results, theoretical or mathematical research results, algorithms suitable for processing data, or the like, or a combination thereof. The conventional device 133 may include a cardiovascular signal measuring device, such as a mercury sphygmomanometer. A peripheral device 134 may be configured to monitor and/or detect one or more types of variables including, for example, temperature, humidity, user or subject input, or the like, or a combination thereof. The above mentioned examples of the external data sources 130 and data types are provided for illustration purposes, and not intended to limit the scope of the present disclosure. For instance, the external data sources 130 may include other sources and other types of data, such as genetic information relating to a subject or his family.

The terminal 140 in the system 100 may be configured for processing at least some of the measured signals, estimating a physiological parameter of interest based on the measured cardiovascular signals, displaying a result including the physiological parameter of interest in the form of, for example, an image, storing data, controlling access to the system 100 or a portion thereof (for example, access to the personal data stored in the system 100 or accessible from the system 100), managing input-output from or relating to a subject, or the like, or a combination thereof. The terminal 140 may include, for example, a mobile device 141 (for example, a smart phone, a tablet, a laptop computer, or the like), a personal computer 142, other devices 143, or the like, or a combination thereof. Other devices 143 may include a device that may work independently, or a processing unit or processing module assembled in another device (for example, an intelligent home terminal). Merely by way of example, the terminal 140 includes a CPU or a processor in a measuring device 110. In some embodiments, the terminal 140 may include an engine 200 as described in FIG. 2, and the terminal 140 may also include a measuring device 110.

The network 150 may be a single network or a combination of different networks. For example, the network 150 may be a local area network (LAN), a wide area network (WAN), a public network, a private network, a proprietary network, a Public Telephone Switched Network (PSTN), the Internet, a wireless network, a virtual network, or any combination thereof. The network 150 may also include various network access points, for example, wired or wireless access points such as base stations or Internet exchange points (not shown in FIG. 1), through which a data source or any component of the system 100 described above may connect to the network 150 in order to transmit information via the network 150.

Various components of or accessible from the system 100 may include a memory or electronic storage media. Such components may include, for example, the measuring device 110, the server 120, the external data sources 130, the terminal 140, peripheral equipment 240 discussed in connection with FIG. 2, or the like, or a combination thereof. The memory or electronic storage media of any component of the system 100 may include one or both of a system storage (for example, a disk) that is provided integrally (i.e. substantially non-removable) with the component, and a removable storage that may be removably connected to the component via, for example, a port (for example, a USB port, a firewire port, etc.) or a drive (for example, a disk drive, etc.). The memory or electronic storage media of any component of the system 100 may include or be connectively operational with one or more virtual storage resources (for example, cloud storage, a virtual private network, and/or other virtual storage resources).

The memory or electronic storage media of the system 100 may include a dynamic storage device configured to store information and instructions to be executed by the processor of a system-on-chip (SoC, for example, a chipset including a processor), other processors (or computing units), or the like, or a combination thereof. The memory or electronic storage media may also be used to store temporary variables or other intermediate information during execution of instructions by the processor(s). Part of or the entire memory or electronic storage media may be implemented as Dual In-line Memory Modules (DIMMs), and may be one or more of the following types of memory: static random access memory (SRAM), Burst SRAM or Synch-Burst SRAM (BSRAM), dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDECSRAM, PCIOO SDRAM, Double Data Rate SDRAM (DDR SDRAM), Enhanced SDRAM (ESDRAM), SyncLink DRAM (SLDRAM), Direct Rambus DRAM (DRDRAM), Ferroelectric RAM (FRAM), or any other type of memory device. The memory or electronic storage media may also include read-only memory (ROM) and/or another static storage device configured to store static information and instructions for the processor of the SoC and/or other processors (or computing units). Further, the memory or electronic storage media may include a magnetic disk, optical disc or flash memory devices to store information and instructions.

In some embodiments, the SoC may be part of a core processing or computing unit of a component of or accessible from the system 100. The SoC may be configured to receive and process input data and instructions, provide output and/or control other components of the system. In some embodiments, the SoC may include a microprocessor, a memory controller, a memory, and a peripheral component. The microprocessor may further include a cache memory (for example, SRAM), which along with the memory of the SoC may be part of a memory hierarchy to store instructions and data. The microprocessor may also include one or more logic modules such as a field programmable gate array (FPGA) or other logic array. Communication between the microprocessor in the SoC and memory may be facilitated by the memory controller (or chipset), which may also facilitate in communicating with the peripheral component, such as a counter-timer, a real-time timer, a power-on reset generator, or the like, or a combination thereof. The SoC may also include other components including, for example, a timing source (for example, an oscillator, a phase-locked loop, or the like), a voltage regulator, a power management circuit, or the like, or a combination thereof.

Merely by way of example, the system 100 may include a wearable or portable device. The wearable or portable device may include a SoC and a plurality of sensors. Exemplary sensors may include a photoelectric sensor, a conductance sensor, or the like, or a combination thereof. The SoC may process signals acquired through at least some of the plurality of sensors. The acquired signals may be various physiological signals including, for example, photoplethysmograph (PPG), electrocardiograph (ECG), or the like, or a combination thereof. The SoC may calculate a physiological parameter of interest based on the acquired signals. Exemplary physiological parameters of interest may be blood pressure, or the like, or a combination thereof.

In some embodiments, the external data source 130 may receive data from the measuring device 110, the sever 120, the terminal 140, or the like, or any combination by the network 150. Merely by way of example, the external data source 130 (for example, a medical institution, or a smart home system, or the like) may receive information relating to a subject (for example, location information, data from the cloud sever or a terminal, or the like, or a combination thereof) based on the data received from the measuring devices 110 or the terminals 140. In some embodiments, the measuring device 110 may receive data from the sever 120, the external data source 130, or the like, or any combination, via the network 150. Merely by way of example, the measuring device 110 may receive the information relating to a subject (for example, a current/historical health condition of a subject, medications the subject is taking, medical treatment the subject is undertaking, current/historical diets, current emotion status, historical physiological parameters (for example, PTT, SBP, DBP) relating to the subject, or the like, or a combination thereof). Furthermore, the terminal 140 may receive data from the measuring device 110, the server 120, the external data source 130, or the like, or a combination thereof.

FIG. 1 is a specific example of the system 100, and the configuration of the system 100 is not limited to that illustrated in FIG. 1. For example, a server 120 may be omitted, migrating all of its functions to a terminal 140. In another example, a server 120 and a terminal 140 may both be omitted, migrating all of their functions to a measuring device 110. The system may include various devices or combinations of devices in different embodiments.

In an example, the system may include a wearable or portable device and a mobile device (for example, a smart phone, a tablet, a laptop computer, or the like). The wearable or portable device may be used to acquire physiological signals, environmental information, or the like, or a combination thereof. The mobile device may be used to receive the signals or information acquired by the wearable or portable device. The mobile device may calculate one or more physiological parameters of interest based on the acquired signals or information, as well as relevant data retrieved from another source (for example, from a server). The retrieved relevant data may include, for example, current/historical information stored on the server. Exemplary current/historical information may include a current/historical health condition of a subject, current/historical medications the subject is/was taking, current/historical medical treatment the subject is/was undertaking, current/historical diets, current/historical emotion status, current/historical physiological parameters (for example, PTT, SBP, DBP) relating to the subject, or the like, or a combination thereof. The wearable or portable device, or the mobile device may display or report, or store at least some of the acquired signals, information, the retrieved relevant data, the calculated one or more physiological parameters of interest, or the like, or a combination thereof. The display or report may be provided to a subject, a user other than the subject, a third party, the server, or another device.

In another example, the system may include a wearable or portable device that may be configured to perform functions including: acquiring physiological signals or environmental information, retrieving relevant data from another source (for example, from a server), calculating one or more physiological parameters of interest based on the acquired signals, information, or the retrieved relevant data, and displaying, reporting, or storing at least some of the acquired signals, information, the retrieved relevant data, the calculated one or more physiological parameters of interest, or the like, or a combination thereof. The display or report may be provided to a subject, a user other than the subject, a third party, the server, or another device.

In a further example, the system may include a wearable or portable device that may be configured to perform functions including: acquiring physiological signals and environmental information, communicating with a server to transmit at least some of the acquired signals or information to the server such that the server may calculate one or more physiological parameters of interest, receiving the calculated one or more physiological parameters of interest from the server, displaying, reporting or storing at least some of the acquired signals, information, the calculated one or more physiological parameters of interest, or the like, or a combination thereof. The display or report may be provided to a subject, a user other than the subject, a third party, the server, or another device. In some embodiments, the communication between the wearable or portable device and the server may be achieved by way of the wearable or portable device being connected to a network (for example, the network 150). In some embodiments, the communication between the wearable or portable device and the server may be achieved via a communication device (for example, a mobile device such as a smart phone, a tablet, a laptop computer, or the like) that communicates with both the wearable or portable device and the server.

In still a further example, the system may include a wearable or portable device, a mobile device (for example, a smart phone, a tablet, a laptop computer, or the like), and a server. The wearable or portable device may be used to acquire physiological signals, environmental information, or the like, or a combination thereof. The mobile device may be used to receive the signals or information acquired by the wearable or portable device, and may calculate one or more physiological parameters of interest based on the received signals and/or information retrieved from the wearable or portable device, as well as relevant data retrieved from another source (for example, a server). The mobile device may display, report, or store at least some of the acquired signals, information, the retrieved relevant data, the calculated one or more physiological parameters of interest, or the like, or a combination thereof. The display or report may be provided to a subject, a user other than the subject, a third party, the server, or another device.

In some embodiments, the system may be configured to provide a user interface to allow a subject, a user other than the subject, or an entity to exchange information (including input into or output from the system) with the system as disclosed herein. The user interface may be implemented on a terminal device including, for example, a mobile device, a computer, or the like, or a combination thereof. The access to the system may be allowed to one who has an appropriate access privilege. An access privilege may include, for example, a privilege to read some or all information relating to a subject, update some or all information relating to a subject, or the like, or a combination thereof. The access privilege may be associated with or linked to a set of login credentials. Merely by way of example, the system may provide three tiers of access privileges. A first tier may include a full access privilege regarding information relating to a subject, allowing both receiving and updating information relating to a subject. A second tier may include a partial access privilege regarding information relating to a subject, allowing receiving and updating part of information relating to a subject. A third tier may include a minimal access privilege regarding information relating to a subject, allowing receiving or updating part of information relating to a subject Different login credentials may be associated with different access privilege to the information relating to a subject in the system. As used herein, updating may include providing information that does not exist in the system, or modifying pre-existing information with new information.

Merely by way of example, the system may receive information relating to a subject provided via the user interface. The information relating to a subject may include basic information and optional information. Exemplary basic information may include the height, the weight, the age (or the date of birth), the gender, the arm length, the nationality, the occupation, a habit (for example, a health-related habit such as an exercise habit), the education background, a hobby, the marital status, religious belief, a health-related history (for example, whether a subject has a history of smoking, a food allergy, a drug allergy, a medical treatment history, a family health history, a history of genetic disease, information regarding a prior surgery, or the like, or a combination thereof), contact information, emergency contact, or the like, or a combination thereof. Exemplary optional information may include, current health condition of the subject, medications the subject is taking, a medical treatment the subject is undertaking, diet. The system may receive, via the user interface, information relating to a specific measurement of, for example, a physiological parameter of interest. Examples of such information may include the motion state of the subject at or around the acquisition time (defined elsewhere in the present disclosure), the emotional state at or around the acquisition time, the stress level at or around the acquisition time, or the like, or a combination thereof. The system may receive, via the user interface, one or more options or instructions. In some embodiments, the options or instructions may be provided by a subject or a user other than the subject answering questions or making selections in response to questions or prompts by the system. In one example, the options or instructions may include a measurement frequency (for example, once a week, once a month, twice a week, twice a month, once a day, twice a day, or the like), a preferred format of the presentation of information to the subject or a user other than the subject (for example, email, a voice message, a text message, an audio alert, haptic feedback, or the like, or a combination thereof). In another example, the options or instructions may include information relating to calculating parameters of interest, for example, rules regarding how to select a model, a function, calibration data, or the like, or a combination thereof.

In some embodiments, the system may provide, via the user interface, information to a subject, or a user other than the subject. Exemplary information may include an alert, a recommendation, a reminder, or the like, or a combination thereof. In one example, an alert may be provided or displayed to the subject or a user other than the subject if a triggering event occurs. Exemplary triggering events may be that at least some of the acquired information or a physiological parameter of interest exceeds a threshold. Merely by way of example, a triggering event may be that the acquired heart rate exceeds a threshold (for example, higher than 150 beats per minute, lower than 40 beats per minute, or the like). As another example, a triggering event may be that the physiological parameter of interest, for example, an estimated blood pressure, exceeds a threshold. In another example, a recommendation may be provided or displayed to the subject or a user other than the subject. Exemplary recommendations may be a request to input specific data (for example, basic information, optional information, updated parameters of interest, updated models, updated functions, updated options and instructions, or the like, or a combination thereof). A reminder may be provided or displayed to the subject or a user other than the subject. Exemplary reminders may include a reminder to take a prescription medication, take a rest, take a measurement of a physiological parameter of interest, or the like, or a combination thereof.

In some embodiments, the system may communicate with the subject, a user other than the subject, and/or a third party through the user interface. Exemplary third parties may be a doctor, a healthcare worker, a medical institution, a research facility, a peripheral device of the subject or a user well-connected to the subject, or the like. Exemplary communications may relate to health conditions of the subject, a dietary habit, an exercise habit, a prescription medication, instructions or steps to conduct a measurement, or the like, or a combination thereof. In some embodiments, a user interface accessible to or by a third party may be the same as, or different from a user interface accessible to or by a subject. In one example, an output or data may be transmitted to a third party (for example, a computer, a terminal at a doctor's office, a hospital where a health care provider is located and the health condition of the subject is being monitored, or the like, or a combination thereof). The third party may provide feedback information or instructions related to the output information via the user interface. Merely by way of example, a third party may receive information regarding one or more physiological parameters of interest relating to a subject, and accordingly provide a recommendation of actions to be taken by the subject (for example, to take a prescription medication, to take a rest, to contact or visit the third party, or the like, or a combination thereof); the system may relay the recommendation to the subject.

Figure 2:
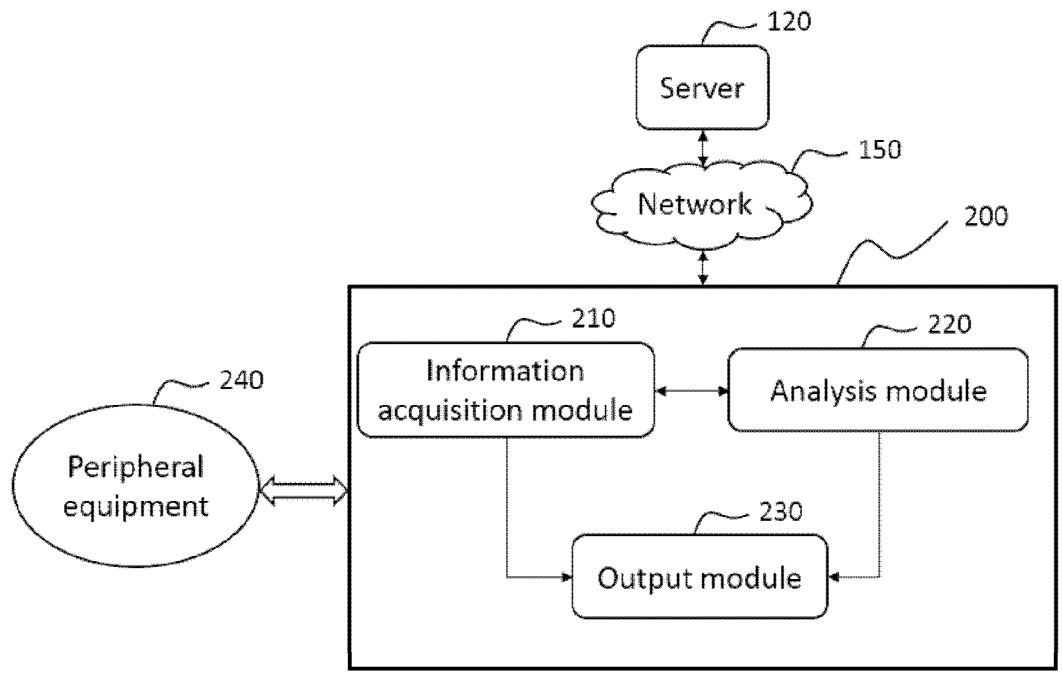
FIG. 2 depicts an exemplary diagram of an engine of the system illustrated in FIG. 1, according to some embodiments of the present disclosure.

FIG. 2 shows an exemplary diagram including the engine 200. The engine 200 may be configured for acquiring one or more signals and calculating or estimating one or more physiological parameters of interest based on the acquired signals. As illustrated, the engine 200 may be connected to or otherwise communicate with, for example, peripheral equipment 240, and the server 120. The engine 200 may include an information acquisition module 210, an analysis module 220, and an output module 230. The information acquisition module 210 may be configured for acquiring a signal or information relating to a subject, for example, a physiological signal, information relating to the health condition of the subject, or the like, or a combination thereof. The analysis module 220 may be configured for analyzing the acquired signal or information, or determining or estimating a physiological parameter of interest, or both. The output module 230 may be configured for outputting the acquired signal or information, the physiological parameter of interest, or the like, or a combination thereof. As used herein, a module may have an independent processor, or use system shared processor(s). The processor(s) may perform functions according to instructions related to various modules. For example, the analysis module 220, according to relevant instructions, may retrieve acquired signals and perform calculations to obtain one or more physiological parameter of interest.

The information acquisition module 210 may be configured for acquiring a signal or information from or relating to one or more subjects. As used herein, acquiring may be achieved by way of receiving a signal or information sensed, detected, or measured by, for example, a sensor, or by way of receiving an input from a subject or from a user other than the subject (for example, a doctor, a care provider, a family member relating to the subject, or the like, or a combination thereof). For brevity, an acquired signal or information may be referred to as acquired information. As used herein, information may include a signal relating to a subject that is acquired by a device including, for example, a sensor, environmental information that is acquired by a device including, for example, a sensor, information that is acquired otherwise including, for example, from an input by a subject or a user other than the subject, a processed or pre-treated information that is acquired as described, or the like, or a combination thereof. Exemplary sensors may include an electrode sensor, an optical sensor, a photoelectric sensor, a pressure sensor, an accelerometer, a gravity sensor, a temperature sensor, a moisture sensor, or the like, or a combination thereof.

Exemplary acquired information may include physiological information. In the exemplary context of determining blood pressure, the physiological information may include a cardiovascular signal. Exemplary cardiovascular signals may include a photoplethysmogram (PPG) signal, an electrocardiogram (ECG) signal, a ballistocardiogram (BCG) signal, a blood pressure (BP), a systolic blood pressure (SBP), a diastolic blood pressure (DBP), a pulse rate (PR), a heart rate (HR), a heart rate variation (HRV), cardiac murmur, blood oxygen saturation, a density of blood, a pH value of the blood, a bowel sound, a brainwave, a fat content, a blood flow rate, or the like, or a combination thereof. Exemplary acquired information may include information regarding a subject, for example, the height, the weight, the age, the gender, the body temperature, the arm length, an illness history, or the like, or a combination thereof. Exemplary acquired information may include information from or relating to the ambient surrounding a subject (referred to as environmental information) at or around the acquisition time. Exemplary environmental information may include temperature, humidity, air pressure, an air flow rate, an ambient light intensity, or the like, or a combination thereof. As used herein, the acquisition time may refer to a time point or a time period when information relating to the subject, for example, physiological information of the subject, is acquired.

The information acquisition module 210 may be configured to receive or load information from the peripheral equipment 240, the server 120, or other devices (not shown) including, for example, an ECG monitor, a PPG monitor, a respiratory monitor, a brainwave monitor, a blood glucose monitor, and a device having similar functions. Examples of peripheral equipment 240 may include a smart watch, an earphone, a pair of glasses, a bracelet, a necklace, or the like, or a combination thereof. The peripheral equipment 240, the server 120, or other devices may be local or remote. For example, the server 120 and the engine 200 may be connected through a local area network (LAN), or Internet. The peripheral equipment 240 and the engine 200 may be connected through a local area network, or Internet. Other devices and the engine 200 may be connected through a local area network, or Internet. The information transmission between the information acquisition module 210 and the peripheral equipment 240, the server 120, or such other devices may be via a wired connection, a wireless connection, or the like, or a combination thereof.

The information acquisition module 210 may be configured to receive information provided by a subject or a user other than the subject via, for example, an input device. The input device may include but is not limited to a keyboard, a touch screen (for example, with haptics or tactile feedback), a speech input device, an eye tracking input device, a brain monitoring system, or the like, or a combination thereof. The information received through the input device may be transmitted to a processor, via, for example, a bus, for further processing. The processor for further processing the information obtained from the input device may be a digital signal processor (DSP), a SoC (system on the chip), or a microprocessor, or the like, or the combination thereof. Other types of input device may include cursor control device, such as a mouse, trackball, or cursor direction keys to convey information about direction and/or command selections, for example, to the processor.

The description of the information acquisition module 210 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, a storage unit (not shown in FIG. 2) may be added to the information acquisition module 210 for storing the acquired information.

The analysis module 220 may be configured for analyzing acquired information. The analysis module 220 may be connected to or otherwise communicate with one or more information acquisition modules 210-1, 210-2, . . . , 210-N to receive at least part of the acquired information. The analysis module 220 may be configured for performing one or more operations including, for example, a pre-treatment, a calculation, a calibration, a statistical analysis, or the like, or a combination thereof. Any one of the operations may be performed based on at least some of the acquired information, or an intermediate result from another operation (for example, an operation performed by the analysis module 220, or another component of the system 100). For instance, the analysis may include one or more operations including pre-treating at least part of the acquired information, identifying a characteristic point or feature of the acquired information or the pre-treated information, calculating an intermediate result based on the identified characteristic point or feature, performing a calibration, analyzing the information regarding the subject provided by the subject or a user other than the subject, analyzing the information regarding the ambient environment surrounding the subject at or around the acquisition time, estimating a physiological parameter of interest, or the like, or a combination thereof.

Some operations of the analysis may be performed in parallel or in series. As used herein, a parallel performance may indicate that some operations of the analysis may be performed at or around the same time; a serial performance may indicate that some operations of the analysis may commence or be performed after other operations of the analysis. In some embodiments, at least two operations of an analysis may be performed in parallel. In some embodiments, at least two operations of an analysis may be performed in series. In some embodiments, some of the operations of an analysis may be performed in parallel, and some of the operations may be performed in series.

The analysis, or some operations of the analysis, may be performed real time, i.e. at or around the acquisition time. The analysis, or some operations of the analysis, may be performed after a delay since the information is acquired. In some embodiments, the acquired information is stored for analysis after a delay. In some embodiments, the acquired information is pre-treated and stored for further analysis after a delay. The delay may be in the order of seconds, or minutes, or hours, or days, or longer. After the delay, the analysis may be triggered by an instruction from a subject or a user other than the subject (for example, a doctor, a care provider, a family member relating to the subject, or the like, or a combination thereof), an instruction stored in the system 100, or the like, or a combination thereof. Merely by way of example, the instruction stored in the system 100 may specify the duration of the delay, the time the analysis is to be performed, the frequency the analysis is to be performed, a triggering event that triggers the performance of the analysis, or the like, or a combination thereof. The instruction stored in the system 100 may be provided by a subject or a user other than the subject. An exemplary triggering event may be that at least some of the acquired information or a physiological parameter of interest exceeds a threshold. Merely by way of example, a triggering event may be that the acquired heart rate exceeds a threshold (for example, higher than 150 beats per minute, lower than 40 beats per minute, or the like). As used herein, "exceed" may be larger than or lower than a threshold. As another example, a triggering event may be that the physiological parameter of interest, for example, an estimated blood pressure, exceeds a threshold.

The analysis module 220 may be centralized or distributed. A centralized analysis module 220 may include a processor (not shown in FIG. 2). The processor may be configured for performing the operations. A distributed analysis module 220 may include a plurality of operation units (not shown in FIG. 2). The operation units may be configured for collectively performing the operations of a same analysis. In the distributed configuration, the performance of the plurality of operation units may be controlled or coordinated by, for example, the server 120.

The acquired information, an intermediate result of the analysis, or a result of the analysis (for example, a physiological parameter of interest) may be analog or digital. In an exemplary context of blood pressure monitoring, the acquired information, an intermediate result of the analysis, or a result of the analysis (for example, a physiological parameter of interest) may include, for example, a PPG signal, an ECG signal, a BCG signal, a BP, a SBP, a DBP, a PR, a HR, a HRV (heart rate variation), cardiac murmur, blood oxygen saturation, a blood density, a pH value of the blood, a bowel sound, a brainwave, a fat content, a blood flow rate, or the like, or a combination thereof.

A result of the analysis, for example, a physiological parameter of interest regarding a subject, may be influenced by various factors or conditions including, for example, an environmental factor, a factor due to a physiological condition of a subject, a factor due to a psychological condition of a subject, or the like, or a combination thereof. One or more of such factors may influence the accuracy of the acquired information, the accuracy of an intermediate result of the analysis, the accuracy of a result of the analysis, or the like, or a combination thereof. For instance, a physiological parameter of interest may be estimated based on a correlation with the acquired information; a factor due to a physiological condition may cause a deviation from the correlation; the factor may influence the accuracy of the physiological parameter of interest that is estimated based on the correlation. Merely by way of example, a cardiovascular signal relating to a subject may vary with, for example, time, the psychological condition of the subject, the psychological condition of the subject, or the like, or a combination thereof. The correlation between a cardiovascular signal with a physiological parameter of a subject may vary with, for example, the physiological condition of the subject, the psychological condition of the subject, the ambient surrounding the subject, or the like, or a combination thereof. Such an influence may be counterbalanced in the analysis.

In an analysis, information relating to an influencing condition (for example, environmental information, a physiological condition, a psychological condition, or the like) may be acquired, and a correction or adjustment may be made accordingly in the analysis. Merely by way of example, the correction or adjustment may be by way of a correction factor. For instance, an environmental correction factor may be introduced into the analysis based on acquired environmental information from or relating to the ambient surrounding a subject at or around the acquisition time. Exemplary environmental information may include one or more of temperature, humidity, air pressure, an air flow rate, an ambient light intensity, or the like. Exemplary environmental correction factors may include one or more of a temperature correction factor, a humidity correction factor, an air pressure correction factor, an air flow rate correction factor, an ambient light intensity correction factor, or the like. As another example, the correction or adjustment may be by way of performing a calibration of the correlation (for example, a calibrated model, a calibrated function, or the like) used to estimate the physiological parameter of interest. As a further example, the correction or adjustment may be by way of choosing, based on information relating to an influencing condition, a correlation from a plurality of correlations used to estimate the physiological parameter of interest.

This description of the analysis module 220 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, a cache unit (not shown in FIG. 2) may be added to the analysis module 220 used for storing an intermediate result or real time signal or information during the processes above mentioned.

The output module 230 may be configured for providing an output. The output may include a physiological parameter of interest, at least some of the acquired information (for example, the acquired information that is used in estimating the physiological parameter of interest), or the like, or a combination thereof. The transmission of the output may be via a wired connection, a wireless connection, or the like, or a combination thereof. The output may be transmitted real-time once the output is available for transmission. The output may be transmitted after a delay since the output is available for transmission. The delay may be in the order of seconds, or minutes, or hours, or days, or longer. After the delay, the output may be triggered by an instruction from a subject, a user other than the subject, or a related third party, an instruction stored in the system 100, or the like, or a combination thereof. Merely by way of example, the instruction stored in the system 100 may specify the duration of the delay, the time the output is to be transmitted, the frequency output is to be transmitted, a triggering event, or the like, or a combination thereof. The instruction stored in the system 100 may be provided by a subject or a user other than the subject. An exemplary triggering event may be that the physiological parameter of interest or that at least some of the acquired information exceeds a threshold. Merely by way of example, a triggering event may be that the acquired heart rate exceeds a threshold (for example, higher than 150 beats per minute, lower than 40 beats per minute, or the like). As another example, a triggering event may be that the physiological parameter of interest, for example, an estimated blood pressure, exceeds a threshold.

The output for transmission may be of, for example, an analog form, a digital form, or the like, or a combination thereof. The output may be in the format of, for example, a graph, a code, a voice message, text, video, an audio alert, a haptic effect, or the like, or a combination thereof. The output may be displayed on a local terminal, or transmitted to a remote terminal, or both. A terminal may include, for example, a personal computer (PC), a desktop computer, a laptop computer, a smart phone, a smart watch, or the like, or a combination thereof. Merely by way of example, an output may be displayed on a wearable or portable device a subject wears, and also transmitted to a computer or terminal at a doctor's office or a hospital where a health care provider is located and monitors the health condition of the subject.

The output module 230 may include or communicate with a display device configured to display output or other information to a subject or a user other than the subject. The display device may include a liquid crystal display (LCD), a light emitting diode (LED)-based display, or any other flat panel display, or may use a cathode ray tube (CRT), a touch screen, or the like. A touch screen may include, for example, a resistance touch screen, a capacity touch screen, a plasma touch screen, a vector pressure sensing touch screen, an infrared touch screen, or the like, or a combination thereof.

The peripheral equipment 240 may include any kind of local or remote apparatuses or devices relating to or communicating with the system 100, or a portion thereof. For example, the peripheral equipment 240 may include a storage device, display equipment, a measuring device, an input device, or the like, or a combination thereof.

In some embodiments, a storage module (not shown in FIG. 2) or a storage unit (not shown in FIG. 2) may be integrated in the engine 200. In some embodiments, a storage unit (not shown in FIG. 2) may be integrated in any one of the information acquisition module 210, the analysis module 220, or the output module 230. The storage module (not shown in FIG. 2) or the storage unit (not shown in FIG. 2) may be used for storing an intermediate result, or a result of an analysis. The storage module (not shown in FIG. 2) or the storage unit (not shown in FIG. 2) may be used as a data cache. The storage module (not shown in FIG. 2) or the storage unit (not shown in FIG. 2) may include a hard disk, a floppy disk, selectron storage, RAM, DRAM, SRAM bubble memory, thin film memory, magnetic plated wire memory, phase change memory, flash memory, cloud disk, or the like, or a combination thereof. The storage module (not shown in FIG. 2) or the storage unit (not shown in FIG. 2) may include memory or electronic storage media described in connection with FIG. 1 and elsewhere in the present disclosure.

In some embodiments, the engine 200 does not include a storage module or a storage unit, and the peripheral equipment 240 or the server 120 may be used as a storage device accessible by the engine 200. The server 120 may be a cloud server providing cloud storage. As used herein, cloud storage is a model of data storage where digital data are stored in logical pools, physical storage spanning multiple servers (and often located at multiple locations). The physical environment including, for example, the logical pools, the physical storage spanning multiple servers may be owned and managed by a hosting company. The hosting company may be responsible for keeping the data available and accessible, and the physical environment protected and running. Such cloud storage may be accessed through a cloud service, a web service application programming interface (API), or by applications that utilize the API. Exemplary applications include cloud desktop storage, a cloud storage gateway, a Web-based content management system, or the like, or a combination thereof. The server 120 may include a public cloud, a personal cloud, or both. For example, the acquired information may be stored in a personal cloud that may be accessed after authorization by way of authenticating, for example, a username, a password, a secret code, or the like, or a combination thereof. Non personalized information including, for example, methods or calculation models, may be stored in a public cloud. No authorization or authentication is needed to access the public cloud. The information acquisition module 210, the analysis module 220 and the output module 230 may retrieve or load information or data from the public cloud or the personal clouds. Any one of these modules may be configured to transmit signals and data to the public cloud or personal cloud.

Connection or transmission between any two of the information acquisition module 210, the analysis module 220, and the output module 230 may be via a wired connection, a wireless connection, or the like, or a combination thereof. At least two of these modules may be connected with different peripheral equipment. At least two of these modules may be connected with the same peripheral equipment. The peripheral equipment 240 may be connected with one or more modules via a wired connection, a wireless connection, or the like, or a combination thereof. Those skilled in the art should understand that the above embodiments are only utilized to describe the invention in the present disclosure. There are many modifications and variations to the present disclosure without departing the spirit of the invention disclosed in the present disclosure. For example, the information acquisition module 210 and the output module 230 may be integrated in an independent module configured for acquiring and outputting signals or results. The independent module may be connected with the analysis module 220 via a wired connection, a wireless connection, or the like, or a combination thereof. The three modules in the engine 200 may be partially integrated in one or more independent modules or share one or more units.

The connection or transmission between the modules in the system 100, or between the modules and the peripheral equipment 240, or between the system and the server 120 should not be limited to the descriptions above. All the connections or transmissions may be used in combination or may be used independently. The modules may be integrated in an independent module, i.e. functions of the modules may be implemented by the independent module. Similarly, one or more modules may be integrated on a single piece of peripheral equipment 240. Any one of the connections or transmissions mentioned above may be via a wired connection, a wireless connection, or the like, or a combination thereof. For example, the wired connection or wireless connection may include, for example, a wire, a cable, satellite, microwave, blue tooth, radio, infrared, or the like, or a combination thereof.

The engine 200 may be implemented on one or more processors. The modules or units of the engine 200 may be integrated in one or more processors. For example, the information acquisition module 210, the analysis module 220, and the output module 230 may be implemented on one or more processors. The one or more processors may transmit signals or data with a storage device (not shown in FIG. 2), the peripheral equipment 240, and the server 120. The one or more processors may retrieve or load signals, information, or instructions from the storage device (not shown in FIG. 2), the peripheral equipment 240, or the server 120, and process the signals, information, data, or instructions, or a combination thereof, to calculate one or more physiological parameters of interest. The one or more processors may also be connected or communicate with other devices relating to the system 100, and transmit or share signals, information, instructions, the physiological parameters of interest, or the like with such other devices via, for example, a mobile phone APP, a local or remote terminal, or the like, or a combination thereof.

Figure 3:
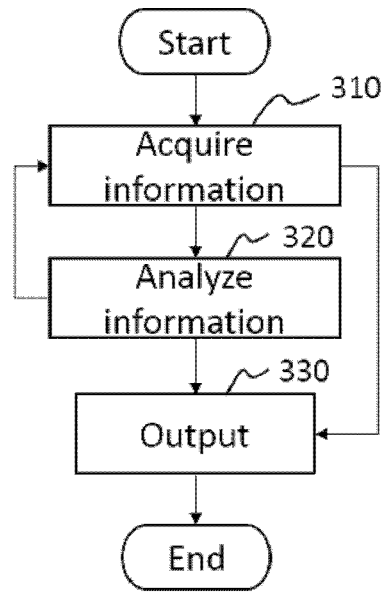
FIG. 3 is a flowchart of an exemplary process in which a method for estimating a physiological signal is deployed, according to some embodiments of the present disclosure.

FIG. 3 is a flowchart showing an exemplary process for estimating a physiological parameter of interest according to some embodiments of the present disclosure. Information regarding a subject may be acquired in step 310. The information acquisition may be performed by the information acquisition module 210. The acquired information may include physiological information of the subject, environmental information relating to the ambient surrounding the subject at or around the acquisition time, information provided by the subject or a user other than the subject. The acquired information may include a PPG signal, an ECG signal, a pulse rate, a heart rate, a heart rate variation, blood oxygen saturation, respiration, muscle state, skeleton state, a brainwave, a blood lipid level, a blood sugar level, the height, the weight, the age, gender, the body temperature, the arm length, an illness history, the room temperature, humidity, air pressure, an air flow rate, the ambient light intensity, or the like, or a combination thereof. At least some of the acquired information may be analyzed at 320. Via the analysis, various features of at least some of the acquired information may be identified. For example, the acquired information may include a PPG signal and an ECG signal; the identified features of these signals may include, for example, waveform, characteristic points, peak points, valley points, amplitude, time intervals, phase, frequencies, cycles, or the like, or a combination thereof. Analysis based on the identified features may be carried out in step 320. For example, the physiological parameter of interest may be calculated or estimated based on the identified features. The physiological parameter of interest estimated based on the acquired PPG signal and ECG signal may include, for example, the BP, the SBP, the DBP, or the like, or a combination thereof. The physiological parameter of interest may be outputted in step 330. Some of the acquired information may be outputted in step 330. The output may be displayed to the subject or a user other than the subject, printed, stored in a storage device or the server 120, transmitted to a device further process, or the like, or a combination thereof. It should be noted that after analysis in step 320, a new acquisition step may be performed in step 310.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, a pre-treatment step may be added between step 310 and step 320. In the pre-treatment step, the acquired signals may be pre-treated, in order to reduce or remove noise or interferences in the signals originally acquired. For example, a sophisticated, real-time digital filtering may be used to reduce or remove high-frequency noise from the PPG or ECG signal, allowing their features to be accurately identified. Exemplary pre-treatment methods may include low-pass filtering, band-pass filtering, wavelet transform, median filtering, morphological filtering, curve fitting, Hilbert-Huang transform, or the like, or a combination thereof. Descriptions regarding methods and systems for reducing or removing noise from a physiological signal, for example, a PPG signal or an ECG signal, may be found in, for example, International Patent Application Nos. PCT/CN2015/077026 filed Apr. 20, 2015, PCT/CN2015/077025 filed Apr. 20, 2015, and PCT/CN2015/079956 filed May 27, 2015, each of which is incorporated by reference. One or more other optional steps may be added between step 310 and step 320, or elsewhere in the exemplary process illustrated in FIG. 3. Examples of such steps may include storing or caching the acquired information.

Figure 4:
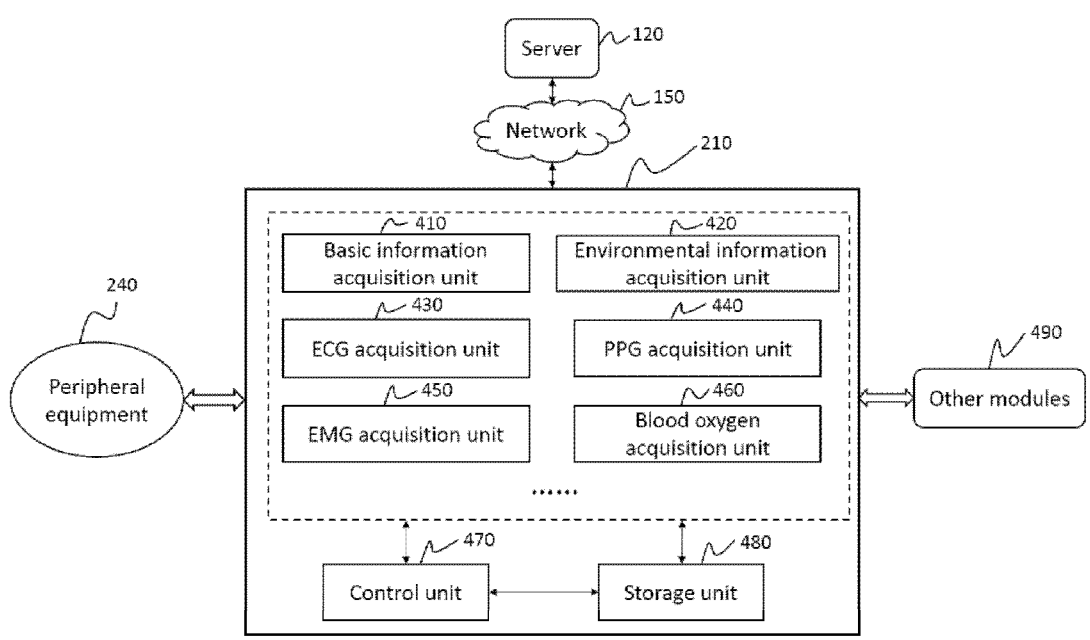
FIG. 4 is a block diagram illustrating an architecture of an acquisition module according to some embodiments of the present disclosure.

FIG. 4 is a block diagram illustrating an architecture of an information acquisition module according to some embodiments of the present disclosure. The information acquisition module 210 may be connected to or otherwise communicate with, for example, the peripheral equipment 240, other modules 490, and the server 120 through the network 150. The information acquisition module 210 may be configured to acquire physiological signals, basic information of a subject, environmental information surrounding the subject, or the like, or a combination thereof. The information acquisition module 210 may include one or more acquisition units (such as a basic information acquisition unit 410, an environmental information acquisition unit 420, an ECG acquisition unit 430, or the like, as shown in FIG. 4), a control unit 470, and a storage unit 480. The one or more acquisition units may be configured for acquiring information relating to a subject, information provided by the subject, a user other than the subject, and/or a related third party (for example, a doctor, a healthcare worker, a medical institution, a research facility, a peripheral device of the subject or a user well-connected to the subject, or the like), environmental information from the ambient surrounding the subject at or around the acquisition time, or the like, or a combination thereof. The one or more acquisition units may include a basic information acquisition unit 410, an environmental information acquisition unit 420, an ECG acquisition unit 430, a PPG acquisition unit 440, an electromyography (EMG) acquisition unit 450, a blood oxygen acquisition unit 460, or the like, or a combination thereof. In some embodiments, the one or more acquisition units may be connected or otherwise communicate with the control unit 470 and the storage unit 480 in real time. The acquisition process may be controlled in real time, and the storage of the acquired information may be performed in real time. In some embodiments, the one or more acquisition units may be connected or otherwise communicate with the control unit 470 and the storage unit 480 after a time delay. The acquisition process may be controlled or modified after a time delay since an acquisition cycle is finished. The storage of the acquired information may be performed after a time delay since the information is acquired. As used in herein, the time delay may be in the order of seconds, or minutes, or hours, or days, or longer, or the like. Similarly the one or more acquisition units may be connected or otherwise communicate with the peripheral equipment 240, or the server 120, or other modules 490 in real time or after a time delay.

The basic information acquisition unit 410 may be configured for receiving the basic information relating to the subject including, for example, the height, the weight, the age (or the date of birth), the gender, the arm length, the nationality, the occupation, a habit (for example, a health-related habit such as an exercise habit), the education background, a hobby, the marital status, religious belief, a health-related history (for example, whether a subject has a history of smoking, a food allergy, a drug allergy, a medical treatment history, a family health history, a history of genetic disease, information regarding a prior surgery, or the like, or a combination thereof), contact information, emergency contact, or the like, or a combination thereof. The basic information relating to the subject may be provided by the subject, a user other than the subject, or a third party (for example, a doctor, a healthcare worker, a medical institution, a research facility, a peripheral device of the subject or a user well-connected to the subject, or the like). The basic information relating to the subject may be loaded from the peripheral equipment 240 or the server 120. The basic information relating to the subject may be stored in the storage unit 480, or may be stored in the server 120, or may be stored in the peripheral equipment 240, or may be stored in a storage device disclosed anywhere in the present disclosure.

The environmental information acquisition unit 420 may be configured for acquiring environmental information surrounding the subject, including temperature, humidity, air pressure, an air flow rate, an ambient light intensity, or the like, or a combination thereof. The environmental information may be acquired in a real time mode (for example, at or around the acquisition time), or may be acquired at a certain time interval (for example, independent of the acquisition time). The environmental information may be loaded from the server 120, or may be loaded from some environment relating APPs (for example, a weather forecast APP). The acquired environmental information may be stored in the storage unit 480, or may be stored in the server 120, or may be stored in the peripheral equipment 240, or may be stored in a storage device disclosed anywhere in the present disclosure.

The ECG acquisition unit 430 may be configured for acquiring the subject's ECG signals by way of an electrode sensing method. The electrode sensing method may be a 12-lead method. The electrode sensing method may be any conventional electrocardiographic lead method. The acquired ECG signals may be stored in the storage unit 480, or may be stored in the server 120, or may be stored in peripheral equipment 240, or may be stored in a storage devices disclosed anywhere in the present disclosure. The acquired signals may be transmitted to other modules 490 (for example, the analysis module 220 or the output module 230) in real time or after a time delay. It should be noted that the ECG acquisition unit 430 may be configured for receiving the subject's ECG signals from a related peripheral device. The related peripheral device may be an ECG monitor, a household ECG monitor, a portable ECG monitor, a medical ECG monitor, or the like, or a combination thereof.

The PPG acquisition unit 440 may be configured for acquiring the subject's PPG signals by way of a photoelectric sensing method. The photoelectric sensing method may be implemented by a single photoelectric sensor, or may be implemented by an array of photoelectric sensors, or may be implemented by a light source and an array of receiving ends. The acquired PPG signals may be stored in the storage unit 480, or may be stored in the server 120, or may be stored in peripheral equipment 240, or may be stored in a storage devices disclosed anywhere in the present disclosure. The acquired PPG signals may be transmitted to other modules 490 (for example, the analysis module 220 or the output module 230) in real time or after a time delay. The PPG acquisition unit 440 may be configured for acquiring the subject's PPG signals from multiple body locations (for example, the head, the neck, the chest, the abdomen, the upper arm, the wrist, the waist, the upper leg, the knee, the ankle, or the like, or a combination thereof). In some embodiments, one or more photoelectric sensors may be placed on any one of the multiple body locations. In some embodiments, one or more photoelectric sensor arrays may be placed on any of the multiple body locations. It should be noted that the PPG acquisition unit 440 may be configured for receiving the subject's PPG signals from a related peripheral device. The related peripheral device may be a PPG monitor, a household PPG monitor, a portable PPG monitor, a medical PPG monitor, or the like, or a combination thereof.

The EMG acquisition unit 450 may be configured for acquiring the subject's EMG signals by way of a pressure sensing method. An electrode patch may be placed on the surface of the body to record a potential change, or an electrode needle may be stick into the body surface to record a local potential change. The blood oxygen acquisition unit 460 may be configured for acquiring the subject's blood oxygen information by way of a photoelectric sensing method. The blood oxygen information may be acquired together with an acquisition of a PPG signal, or may be acquired independently. The acquired EMG signals and blood oxygen information may be stored in the storage unit 480, or may be stored in the server 120, or may be stored in the peripheral equipment 240, or any storage device disclosed anywhere in the present disclosure.

The one or more acquisition units may communicate with one or more sensors to acquire information sensed, detected or measured by the one or more sensors. Exemplary sensors include an electrode sensor, an optical sensor, a photoelectric sensor, a conductance sensor, a pressure sensor, an accelerometer, a gravity sensor, a temperature sensor, a moisture sensor, or the like, or a combination thereof.

Merely by way of example, an optical sensor may include an integrated photodetector, amplifier, and a light source. The light source may emit radiation of wavelengths of, for example, the visible spectrum, the infrared region, or the like, or a combination thereof. The photodetector may detect the reflected radiation. The optical sensor may be placed at a body location on a subject to detect a pulse-related signal of a subject. In one example, multiple wearable PPG sensors may be placed at multiple body locations on a subject. The multiple locations may include the head, the neck, the chest, the abdomen, the upper arm, the wrist, the waist, the upper leg, the knee, the ankle, or the like, or a combination thereof. In another example, a PPG sensor array including a series of PPG sensors may be placed at a body location on a subject. In some embodiments, the PPG sensors may be assembled into one device. The device may be a wearable or portable device including, for example, a T-shirt, a smart watch, a wristband, or the like, or a combination thereof. The device may further include one or more processors or processing units. The processor or the processing unit may be configured for controlling the process of information acquisition, or may be configured for performing one or more operations of any of the modules. Signals or data may be transmitted between sensors placed at different locations. The transmission may be via a wireless connection (for example, wifi, blue tooth, near-field communication (NFC), or the like, or a combination thereof), a wired connection, or the like, or a combination thereof. For example, signals received by the sensors may be transmitted through a wireless body sensor network (BSN) or an intra-body communication (IBC).

The information acquisition module 210 may include other one or more acquisition units other than those described above, such as an acquisition unit (not shown in FIG. 4) configured for acquiring a BCG signal, an acquisition unit (not shown in FIG. 4) configured for acquiring body temperature information of the subject, an acquisition unit (not shown in FIG. 4) configured for acquiring a blood density information of the subject, an acquisition unit (not shown in FIG. 4) configured for acquiring a pH value information of the blood, or the like, or a combination thereof.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the acquisition units may be integrated into an independent unit configured for acquiring more than one information or signal relating to the subject. At least some of the acquisition units may be integrated into one or more independent units.

The control unit 470 may be configured for controlling a factor or a condition during the information acquisition process. The factor or condition may include ON/OFF of the acquisition units, the configuration of information acquisition, a sampling rate, an acquisition cycle, the transformation or processing of the acquired information, the sequence of acquiring different signals, the selection of one or more sensors or sensor arrays, the arrangement of the sensors, the arrangement of a sensor array, the number and/or shape of one or more electrodes of a sensor array, the selection of one or more light sources, the sensitivity or accuracy of a sensor or sensor array, or the like, or a combination thereof.

Merely by way of example, the control unit 470 may be configured for controlling the selection of different PPG sensors or PPG sensor arrays for a signal acquisition process according to some embodiments of the present disclosure. As described above, the sensor configuration in the PPG acquisition unit 440 may be a single photoelectric sensor, or a plurality of photoelectric sensors, or a single sensor array, or a plurality of sensor arrays. A specific sensor configuration may be selected during a specific acquisition process. The selection of a sensor configuration may be performed based on a feature of a subject. Exemplary features may include height, weight, gender, body size, or the like, or a combination thereof. In some embodiments, the selection may be performed through a stepper machine, or through a micro-motor. In some embodiments, the selection may be performed using memory materials (for example, a memory metal). In another example, the control unit 470 may be configured for adjusting a location of a sensor or a sensor array according to the body size of a subject. In another example, the control unit 470 may be configured for adjusting the arrangement of a sensor or a sensor array according to the height or weight of a subject. The process of the adjustment may be performed automatically, or may be performed at least partially manually. For instance, the control unit 470 may calculate or determine, based on the height of a subject, a desirable location of a sensor; the subject, a user other than the subject, and/or a related third party may manually place the sensor or sensor array at the desirable location.

The control unit 470 may include one or more control sub-units (not shown in FIG. 4). In some embodiments, the control sub-units (not shown in FIG. 4) may perform different control functions, respectively. In some embodiments, the control sub-units (not shown in FIG. 4) may be configured for controlling different acquisition units, respectively. In some embodiments, the control sub-units (not shown in FIG. 4) may perform one or more control steps and control the information acquisition in series (for example, a control step performed after another control step at or around the same time). The control unit 470 may include a micro-processor. The micro-processor may be configured to execute one or more instructions provided by the subject, a user other than the subject, and/or a related third party.

The storage unit 480 may be configured for storing acquired information, control factor or condition, or inter-data during the information acquisition. The storage unit 480 may include one or both of a system storage (for example, a disk) that is provided integrally (i.e. substantially non-removable) with the component, and a removable storage that is removably connectable to the component via, for example, a port (for example, a USB port, a firewire port, etc.) or a drive (for example, a disk drive, etc.). The storage unit 480 may include or be connectively operational with one or more virtual storage resources (for example, cloud storage, a virtual private network, and/or other virtual storage resources). The storage unit 480 may include a hard disk, a floppy disk, selectron storage, RAM, DRAM, SRAM bubble memory, thin film memory, magnetic plated wire memory, phase change memory, flash memory, cloud disk, or the like, or a combination thereof. The storage unit 480 may be connected or otherwise communicate with other modules 490, the server 120, and the peripheral equipment 240. The storage unit 480 may include memory or electronic storage media described in connection with FIG. 1 and elsewhere in the present disclosure.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage unit 480 is not necessary, the storage may be implemented through other storage media described elsewhere in the present disclosure. The storage unit 480 may be integrated into the acquisition units or may be integrated in the control unit 470.

FIG. 5-A and FIG. 5-B are schematic diagrams showing an exemplary arrangement or location of the ECG sensors and PPG sensors according to some embodiments of the present disclosure. An ECG sensor may be an electrode sensor including one or more electrodes. The one or more electrodes may be used for sensing the potential change indicating the cardiac activity of a subject wearing the sensor. Merely by way of example, an ECG sensor may include 10 electrodes in a 12-lead form for acquiring ECG signals. FIG. 5-A illustrates exemplary locations on the body of a subject where the 10 electrodes of the ECG sensor may be placed according to a 12-lead form. In the 12-lead form, the 10 electrodes may be located on one or more limbs and/or on the he chest of the subject, as shown in FIG. 5-A. For instance, the locations of the 10 electrodes may include the right arm (RA), the left arm (LA), the right leg (RL), the left leg (LL), the fourth intercostal space to the right of the sternum (V1), the fourth intercostal space to the left of the sternum (V2), the fifth intercostal space in the mid-clavicular line (V4), between leads V2 and V4 (V3), horizontally even with V4 in the left anterior axillary line (V5), and horizontally even with V4 and V5 in the mid axillary line (V6). The 10 electrodes may form 12 different leads representing or measuring the electrical potential difference between pairs of body points. In this embodiment, the overall magnitude of the heart's electrical potential may be measured from 12 different angles ("leads"). It is understood that the 12-lead ECG sensor is described for illustration purposes, and not intended for limiting the scope of the present disclosure. An ECG sensor of another form may be used for acquired ECG signals, e.g., a five-lead form. Also see, for example, International Application No. PCT/CN2015/083334 filed Jul. 3, 2015, the entire contents of which are hereby incorporated by reference.

According to some embodiments of the present disclosure, the PPG sensor may be a photoelectric sensor. FIG. 5-B illustrates the locations on the body of a subject where the photoelectric sensors may be placed. The photoelectric sensor may include an emitting end for emitting a light source and a receiving end used for acquiring a signal resulting from the emitted light source. The acquired signal may be used to derive or provided a PPG value. For brevity, a PPG signal, as used herein, may refer to the derived PPG value, or the acquired signal used to derive the PPG value. The light source may include a light source of a suitable wavelength including, for example, red, green, blue, infra-red, purple, yellow, orange, or the like, or a combination thereof. The spectrum of the light sources may include visible spectrum, infrared spectrum, far-infrared spectrum, or the like, or a combination thereof. The receiving end may be a detector that may detect the quantity of the received signals and/or a change thereof, and/or provide a corresponding output (for example, an electrical signal or an optical signal).

As shown in FIG. 5-B, the photoelectric sensors may be placed on or at multiple body locations of a subject. The locations may include the head, the neck, the chest, the abdomen, the upper arm, the wrist, the waist, the upper leg, the knee, the ankle, or the like, or a combination thereof. The photoelectric sensors placed on or at multiple body locations may be used for acquiring multiple PPG signals including the pulse related information of the corresponding body locations. Merely by way of example, the light source of the photoelectric sensor placed on the head of the subject may emit one or more light signals to the nearby blood vessels and the receiving end may acquire one or more signals resulting from the emitted light source. In some embodiments, the acquired signal may be or relate to a PPG signal indicating a pulse or blood related information of the head or a portion thereof. In some embodiments, the acquired PPG signal may be used for calculating a physiological parameter of interest (for example, blood pressure) indicating a health condition of the head, or a portion thereof, of the subject. In some embodiments, a variation of the PPG wave may indicate a variation of the blood vessel(s) or a variation of the blood viscosity of the nearby location of the head, or a portion thereof, of the subject. Similarly, blood related information of other body locations may be acquired by one or more photoelectric sensors placed on one or more body locations.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, in addition to the location configuration shown in FIG. 5-B, one or more photoelectric sensors may be added to other body locations. On a body location, a sensor array other than an independent sensor may be placed (will be described in detail in FIG. 6).

FIG. 6-A through FIG. 6-D are schematic diagrams showing exemplary sensor arrays according to some embodiments of the present disclosure. A sensor array may include a plurality of portions. A portion of the sensor array may be a sensor, or a receiving end of a sensor, or an emitting end of a sensor. As shown in FIG. 6-A through FIG. 6-D, the portions of the sensor array may be arranged in an oval array, a rectangular array, a rhombus array, a circular array, or the like, or a combination thereof.

In some embodiments, a portion of the sensor array may be a sensor. The sensor array may include one or more types of sensors. For instance, a sensor array may include at least one photoelectric sensor and at least another type of sensor. In one example, the sensor array may include a series of PPG sensors. The sensor array may be configured for acquiring a series of PPG signals.

In some embodiments, a portion of the sensor array may be a receiving end of a sensor. The sensor array may include one or more receiving ends. The one or more receiving ends may be configured for receiving signals based on a same light source, or based on different light sources. The light sources may be emitted by one or more emitting end of a sensor. The one or more emitting ends may be integrated in the sensor array, or located outside of the sensor array, or located in any module or unit of the system. In one example, during the detection of PPG signals, the one or more emitting ends may emit a series of light signals simultaneously or successively toward a location of interest. Thus the sensor array may acquire a series of signals. In some embodiments, the series of acquired signals may be used to provide a series of PPG signals detected from the body location of interest.

In some embodiments, a portion of the sensor array may be an emitting end of a sensor. The sensor array may include one or more emitting ends. The one or more emitting ends may be configured for emitting a series of lights toward a body location of interest. One or more receiving ends may be integrated in the sensor array, or located outside of the sensor array, or located in a module or a unit nearby the sensor array. The one or more receiving ends may acquire a series of signals based on the series of lights emitted by the series of emitting ends. In some embodiments, the series of the acquired signals may be used to provide a series of PPG signals detected from the body location of interest.

In some embodiments, the signals acquired by a sensor array may be analyzed and/or processed using one or more signal processing methods including, for example, those described in FIG. 8-A through FIG. 8-E. In some embodiments, the acquired signals may be processed or analyzed to generate a new signal. Merely by way of example, the new signal may be the mean value or the average value of the acquired signals. As another example, the signals acquired by a sensor array may include a first acquired signal and a second acquired signal; the first acquired signal may indicate a measurement error; the second acquired signal may include or be affected by the measurement error; the first acquired signal may be used to correct or otherwise modify a second acquired signal. For instance, a series of PPG signals may be acquired using a sensor array. The sensor array may include an emitting end of a PPG sensor that may emit different light signals, and two receiving ends that may acquire PPG signals relating to PPG based on the emitted light signals. A first acquired signal may relate to a measurement error arising from the movement of an internal organ of a subject; a second acquired signal may be a coarse PPG signal including at least part of the measurement error; the first acquired signal and the second acquired signal may be analyzed and processed to generate a new PPG signal that at least part of the measurement error is corrected. The new PPG signal may be used for calculating a physiological parameter of interest in subsequent steps.

FIG. 6-A illustrates an oval array including eleven portions. FIG. 6-B illustrates a rectangular array including nine portions. FIG. 6-C illustrates a rhombus array including nine portions. FIG. 6-D illustrates a circular array including nine portions.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, other than the oval array, the rectangular array, the rhombus array, the circular array, other types of array may be used for the sensor array design. As another example, an oval array may include more than or fewer than eleven portions. As still another example, the locations of the portions may be different from those illustrated in FIG. 6-A through FIG. 6-D. For instance, a rectangular array may be a 3×3 array, a 6×6 array, a 9×9 array, an m×m array, an m×n array in which m may be different from n, or the like, or a combination thereof. In still a further example, a sensor array may include at least two types of sensors. For instance, a sensor array may include a PPG sensor and a temperature sensor.

Figure 7:
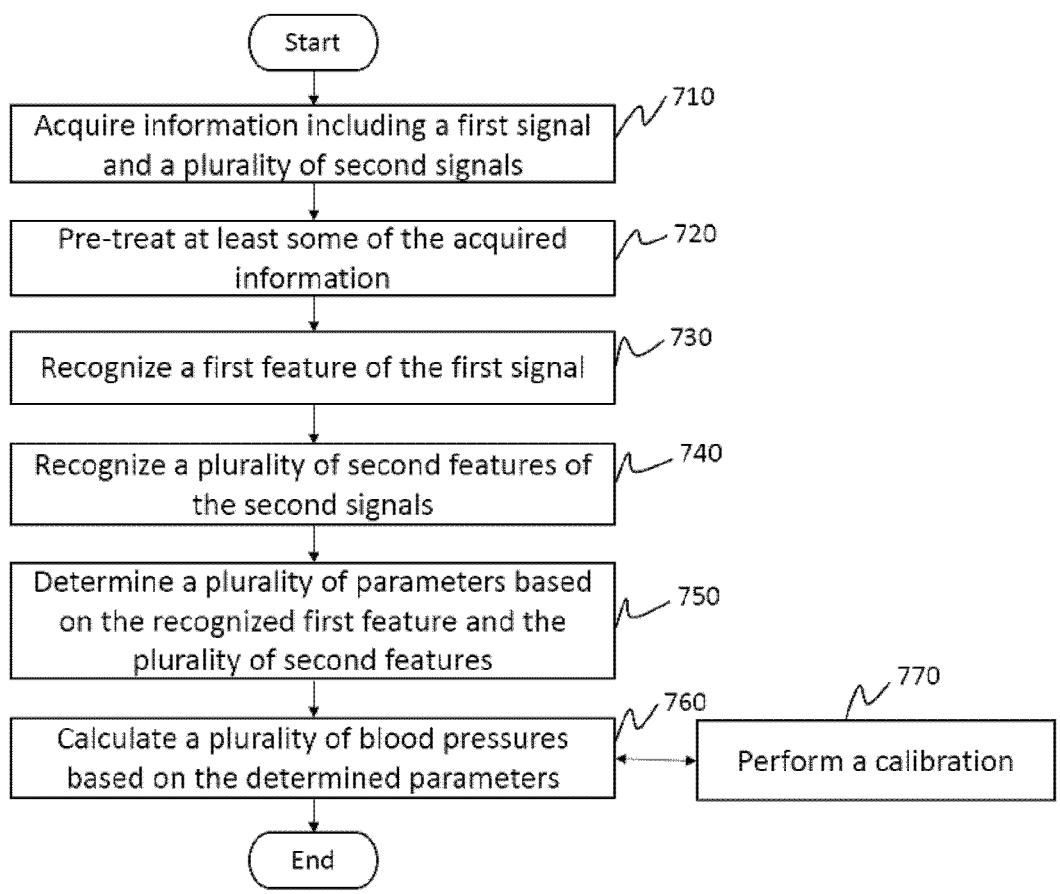
FIG. 7 is a flowchart of a process for estimating a physiological parameter of interest according to some embodiments of the present disclosure.

FIG. 7 is a flowchart of an exemplary process for estimating a blood pressure according to some embodiments of the present disclosure. Beginning in step 710, information including a first signal and one or more a plurality of second signals may be acquired. In some embodiments, a plurality of first signals may be acquired. The acquisition of the signals or related information may be performed by the information acquisition module 210. At least some of the signals or related information may be acquired by one or more sensors. At least some of the sensors may be part of or communicate with the system 100 or a portion thereof. At least some of the signals or related information may be provided by, for example, a subject, a user other than the subject, or a third party. At least some of the signals or related information may be retrieved from the information acquisition module 210, the server 120, the storage unit 480, a storage device anywhere disclosed in the present disclosure, or the like, or a combination thereof. Merely by way of example, the first and the second signals may be physiological signals including, for example, an electrocardiogram (ECG) signal, a pulse-related (or pulse-wave-related) signal (for example, a PPG signal), a phonocardiogram (PCG) signal, an impedance cardiogram (ICG) signal, or the like, or any combination thereof. For example, the first signal may be an ECG signal; the second signal(s) may be a plurality of PPG signals. The ECG signal may be detected in a 12-lead form illustrated in FIG. 5-A. The plurality of second signals may be acquired by a plurality of sensors or sensor arrays. For instance, a plurality of second signals may be acquired using a plurality of sensors, a plurality of sensor arrays placed on multiple body locations of the subject illustrated in FIG. 5-B. As another example, at least one second signal may be acquired using a sensor; at least one second signal may be acquired using a sensor array; the sensor and the sensor array may be placed at a same body location of the subject, or at different body locations of the subject.

In some embodiments, the first signal and the plurality of second signals may be acquired simultaneously, at or around the same time. In some embodiments, the plurality of second signals may be acquired simultaneously, at or around the same time. In some embodiments, the plurality of second signals may be acquired successively.

In step 720, at least some of the acquired information may be pre-treated. In some embodiments, the acquired first signal and/or the acquired plurality of second signals may be pre-treated. The pre-treatment may be performed to reduce or remove noise or interferences in the signals or signal related data. The pre-treatment may be performed by the analysis module 220. Exemplary methods that may be used in the pre-treatment may include low-pass filtering, band-pass filtering, wavelet transform, median filtering, morphological filtering, curve fitting, Hilbert-Huang transform, or the like, or any combination thereof. During the process of the pre-treatment, the methods mentioned herein may be used in parallel or may be used in combination. Descriptions regarding methods and systems for reducing or removing noise from a physiological signal, for example, a PPG signal or an ECG signal, may be found in, for example, International Patent Application Nos. PCT/CN2015/077026 filed Apr. 20, 2015, PCT/CN2015/077025 filed Apr. 20, 2015, and PCT/CN2015/079956 filed May 27, 2015, each of which is incorporated by reference. Additionally, real-time transformation of time domain or frequency domain may also be implemented in step 720, and the signals or related information may be used in time domain, frequency domain, or both.

In step 730 and in step 740, a first feature of the first signal and a plurality of second features of the plurality of second signals may be recognized. The recognition of the first feature and the second features may be performed simultaneously, at or around the same time, or may be performed successively. In the exemplary context of blood pressure monitoring, the first signal or the second signals may include an ECG signal, a PPG signal, a BCG signal, or the like; exemplary features of the first signal or the second signals may include waveform, characteristic points, amplitude, phase, frequency, cycle, a first-order moment of a signal, a high-order moment of a signal, a first-order derivative of a signal, a high-order derivative of a signal, or the like, or any combination thereof. The characteristic points may include a peak point, a valley point, a fastest rising point of a wave, a starting point of a wave, an end point of a wave, or the like, or a combination thereof. In some embodiments, the features recognized in step 730 and in step 740 may include a peak point of the R wave on an ECG signal, a maximum positive peak of a PPG signal, a fastest rising point of a PPG signal, a start point of a PPG wave, or the like, or a combination thereof.

In some embodiments, before the recognition of the plurality of second features, the plurality of second signals may be analyzed and processed. In some embodiments, the plurality of second signals may be mathematically processed. One second signal from the plurality of second signals may be used for correcting one or more second signals of the plurality of second signals. The plurality of second signals may be analyzed and processed to generate, one or more new signals (also may be referred to as "a third signal"). In some embodiments, the plurality of second signals may be a plurality of PPG signals acquired by a plurality of sensors and/or sensor arrays placed on multiple body locations of the subject. For example, the plurality of second signals may be multiple PPG signals acquired by multiple PPG sensors located on multiple body locations of the subject. In another example, the plurality of second signals may be multiple series of PPG signals acquired by multiple sensor arrays as illustrated in FIG. 6-A through FIG. 6-D placed on or at multiple body locations of the subject. As used herein, "a series of PPG signals" refers to PPG signals acquired by a sensor array from a body location of the subject. Thus "multiple series of PPG signals" may refer to PPG signals acquired by multiple sensor arrays from multiple body locations of the subject. Exemplary body locations may include the head, the neck, the chest, the abdomen, the upper arm, the wrist, the waist, the upper leg, the knee and the ankle. In some embodiments, a series of PPG signals acquired by a sensor array may be analyzed and processed using one or more signal processing methods including, for example, those described in FIG. 8-A through FIG. 8-E, to generate a new PPG signal. Thus a plurality of new PPG signals may be generated from multiple series of PPG signals. In some embodiments, the new PPG signal may be the mean value or the average value of the plurality of acquired PPG signals. Then a plurality of second features may be recognized from the plurality of new PPG signals in step 740.

In step 750, a plurality of parameters based on the recognized features of the first and the plurality of second signals may be determined. In some embodiments, the parameter may be the pulse transit time (PTT). As used herein, the pulse transit time may refer to the time interval between the characteristic points of an ECG signal and a pulse wave related signal including, for example, a PPG signal. In one example, PTT is determined by a time interval between an ECG fiducial point (typically the R peak, but also the Q/S peak, or even the peak of a P/T wave may be used) and a fiducial point marking the pulse arrival (e.g., a start point of the PPG wave, a fastest rising point, or the like). In another example, PTT is determined by a time interval between two pulse wave signals (e.g., two PPG signals) detected at different body locations, e.g., the carotid and femoral arteries. The plurality of determined parameters may be used for calculating blood pressures in step 760. In some embodiments, blood pressure may be calculated based on the determined PTTs in step 760.

A pre-treatment step may be performed to assess an acquired signal (for example, an ECG signal, a PPG signal, etc.) before one or more features of the signal is identified. For instance, an acquired ECG signal may be accessed before one or more features of the signal is identified. The assessment may be performed to evaluate whether a valid ECG signal is acquired. The assessment may be performed by way of, for example, a pattern recognition process. For instance, the R peak of an acquired ECG signal may be determined by the pattern recognition process. In some embodiments, the system may identify an abnormal signal or waveform (e.g., an abnormal sinus rhythm R wave, another physiological signal, or the like) that may be unsuitable for determining PTT; such an abnormal signal or waveform may be abandoned to avoid to be involved in the subsequent calculation or analysis. In some embodiments, the acquired ECG signal may be compared with a reference signal to determine whether the acquired ECG signal includes an abnormal R wave. The reference signal may be a normal sinus rhythm ECG signal, or may be retrieved from a database having historical data.

The ECG waveform and the PPG waveform are cyclical signals, i.e. the characteristic points occur substantially cyclically or periodically. Thus PTT' is approximated by a time interval of the maximum point on the QRS complex on the ECG waveform and a peak point on a subsequent (second) PPG waveform. Similarly, PTT" also may be approximated by a time interval between the peak point on the QRS complex on the ECG waveform and a peak point on a further (third) PPG waveform. The value of PTT' and the value of PTT" are larger than that of PTT, and errors or deviations may occur while estimating blood pressure or other physiological parameters of interest based on such inaccurate PTT' and PTT" values. Such errors or deviations may be avoided or reduced by using a PPG waveform from the same cycle (driven by the same heart beat) as the ECG waveform. Thus, during recognition of characteristic points of the PPG waveform, a threshold may be set regarding the time window or segment within which the characteristic points on the PPG waveform may be identified and used to determine PTT. In one example, the time window may be 2 seconds or less. Merely by way of example, an analysis to identify a fiduciary point on a PPG waveform is performed on a segment of the PPG waveform occurring within 2 seconds from the time point when the maximum point on the ECG waveform is identified, in order to approximate the PTT. As another example, an analysis to identify a fiduciary point on a PPG waveform is performed on a segment of the PPG waveform occurring between two consecutive peak points on the ECG waveform, in order to approximate the PTT. As a further example, the time window may be set based on the heart rate of the subject. For instance, the time window may be set based on the heart rate of the subject at or around the acquisition time, or an average heart rate of the subject for a period of time, or an average heart rate of a group of people (for example, a sub-group of people who share a same or similar characteristic with the subject; exemplary characteristic may include age, gender, nation, stature, weight, a body fat percentage, color of skin, a family health history, a life style, an exercise habit or other habit, diet, occupation, illness history, education background, marital status, religious belief, or the like, or any combination thereof.

The cycle of ECG or the cycle of PPG may vary. As an example, the cycle of ECG or the cycle of PPG of different subjects may be different. As another example, the cycle of ECG or PPG of the same subject may vary under different situations (e.g., when the subject is exercising or asleep, at different times of a day, at the same or similar time on different days), or the like, or a combination thereof. In one example, the time window threshold may be set based on the heart rate of a subject (for example, the cycle of average person is approximately 60-120 beats per minute). The heart rate may be an average value over a period of time (e.g., a week, a month, a year, or the like). The heart rate may be one measured at or around the acquisition time. The heart rate may be measured based on, e.g., the ECG signal, the PPG signal, or the like. The time window may be set or updated based on the measured heart rate. In another example, the time window may be set by, e.g., the system, the subject, or a user other than the subject, based on the physiological information of the subject. For example, the physiological information may include motion or not, taking medicine or not, good or bad mood, emotional stress or not, or the like, or a combination thereof. In another example, the time window may be a fixed value defined by the system, the subject, or a user other than the subject (e.g., his doctor, health care provider, or the like).

In step 750, a parameter such as PTTV (pulse transit time variation) may be approximated based on a group of determined PTT. A parameter such as HRV may be determined based a group of ΔRR. As used herein, ΔRR refers to as a time interval between two adjacent R waves (the maximum point of a QRS waveform). More descriptions regarding the determination of the PTT may be found in International Patent Application No. PCT/CN2015/083334 filed Jul. 3, 2015, which is hereby incorporated by reference.

In some embodiments, relation information among the plurality of parameters may be generated (not shown in FIG. 7). The relation information may be stored in the server 120, the analysis module 220, or any storage device disclosed anywhere in the present disclosure. In some embodiment, the relation information may provide guidance regarding a compensation term. The compensation term may be added to a model used to calculate a blood pressure in step 760. See, for example, Equation 9. In some embodiments, a relation information among the acquired plurality of second signals may be generated (not shown in FIG. 7). Similarly the relation information may be retrieved to generate a compensation term.

In step 760, a plurality of blood pressure values may be calculated based on the parameter(s) including, for example, the determined PTT, PTTV, HRV, or the like, or a combination thereof. One or more calculation models may be stored in the server 120, the analysis module 220, or any storage device disclosed anywhere in the present disclosure. During the calculation, one or more favorite models may be retrieved based on the subject's personal data, universal data, additional information in a history, or the like, or a combination thereof. As used herein, a favorite model may refer to a model that may provide a more accurate estimation of a physiological parameter of interest from acquired information than one or more other models.

In some embodiments, the plurality of second signals acquired in step 710 may be a plurality of PPG signals acquired from multiple body locations of the subject. Thus in step 760, a plurality of blood pressure values of a plurality of body locations may be calculated based on the plurality of PPG signals. Similarly, in some embodiments, a plurality of physiological parameters of interest of multiple body locations may be calculated. Relation information among the plurality of blood pressures may be generated (not shown in FIG. 7). As described above, in some embodiments, relation information among the determined plurality of parameters or relation information among the plurality of second signals may be generated.

In some embodiments, the relation information may be used to detect whether an error occur during calculating the physiological parameters. For instance, an error of the second signal at one body location may indicate a possible problem with the measurement of at least part of or the entire set of the second signals. As another example, the relation information including the distribution of the second signals at multiple body locations may indicate a pathological condition. For instance, the deviation from a normal distribution of blood pressure derived from the second signals at multiple body locations of a subject may indicate arteriosclerosis.

In some embodiments, a guide information may be generated based on the relation information. The guide information may relate to the selection of calculation models that may be used to calculate the physiological parameter of interest of the subject based on the acquired signals including, for example, the first signal, the second signals, etc. For instance, for a subject with arteriosclerosis and a subject without arteriosclerosis, different calculation models may be used to calculate blood pressure based on PTT values. The guide information may be a modified model used for calculating the physiological parameter of interest of the subject. In some embodiments, the modification may be to include a compensation term. See, for example, Equation 9 described below. The compensation term may relate to the distribution or interrelation of multiple second signals at different body locations of the subject, or information derived from the multiple second signals. For instance, the compensation term may relate to the distribution of PTT values at multiple body locations. The compensation term may be a relationship of the difference between the PTT values at two or more body locations. The relationship may be expressed in the form of a linear function, an nth degree polynomial, an exponential function, a logarithmic function, a trigonometric function, an anti-trigonometric function, a hyperbolic function, or the like, or a combination thereof. For instance, a PTT value at the left arm may be compared to a PTT value at the right arm. The interrelation or difference between the two PTT values may be analyzed to generate a compensation term. As another example, a comparison may be performed among a PPT value at the left upper arm, a PPT value at the right upper arm, a PPT value at the left ankle, and a PPT value at the right ankle; the interrelation or difference between the four PTT values may be analyzed to generate a compensation term.

In some embodiments, the compensation term may relate to one or more PTTV values. For instance, one or more PTTV values may be determined based on a group of determined PTT values at a body location. The compensation term may be the difference between the PTTV values. The relationship may be expressed in the form of a linear function, an nth degree polynomial, an exponential function, a logarithmic function, a trigonometric function, an anti-trigonometric function, a hyperbolic function, or the like, or a combination thereof. In some embodiments, the compensation term may relate to one or more HRV values (as described above). Similarly the compensation term may be a relationship of the difference between the HRV values.

In some embodiments, the compensation term may relate to a combination of a PTTV value, an HRV value, the interrelationship or difference between two or more PTT values of various body locations, or the like. In some embodiments, the compensation term may be a relationship of a PTTV value and an HRV value. In some embodiments, the compensation term may be a relationship of an HRV value and the interrelationship or difference between two or more PTT values of various body locations. In some embodiments, the compensation term may be a relationship of a PTTV value at a body location and the interrelationship or difference between two or more PTT values of various body locations. The relationship may be expressed in the form of a linear function, an nth degree polynomial, an exponential function, a logarithmic function, a trigonometric function, an anti-trigonometric function, a hyperbolic function, or the like, or a combination thereof.

During the process, a calibration may be performed in step 770. The calibration may be performed periodically, upon a subject's instruction, or the like, or a combination thereof. The calibration may take time-varying properties into account. The time-varying properties may include, e.g., the arterial propagation path of a specific subject, the heart activity of a specific subject, the real-time temperature or humidity, the updated fiducial BP of a specific subject, the updated database storing historical data (SBP/DBP values, BP calculating algorithms, etc.) of a specific subject, the updated database storing reference data of people sharing the same or similar characteristics (e.g., age, gender, stature, weight, a body fat percentage, color of skin, a family health history, a life style, an exercise habit, diet, a psychological condition, a health condition, an education history, occupation, or the like, or any combination thereof), or the like, or any combination thereof.

The calibration data may include physiological parameters, information (e.g., environmental or personal information) relating to the physiological parameter, or the like, or a combination thereof. Exemplary physiological parameters may include $PTT_0$, $SBP_0$, $DBP_0$, $PTTV_0$, $HRV_0$, or the like, or a combination thereof. Exemplary models may include different functions or a same function with different coefficients. At least some of the functions may approximate or illustrate a correlation between a physiological parameter of interest and the acquired signals (or some features of the acquired signals). Exemplary functions may include different polynomials, e.g., polynomials of different degrees, polynomials of the same degree with different coefficients, or the like, or a combination thereof. For example, under on specific condition of the localized analysis, only the calibration values (C) occurred within an interval may be considered as suggested in Equation 1:

$$\{C=(PTT_0, Blood\ Pressure_0) | PTT-a<PTT_0<PTT+b\}. \quad \text{Equation 1}$$

In some embodiments, constants a and b in Equation 1 may be pre-defined independently of a specific measurement. In some embodiments, constants a and b in Equation 1 may be determined for a specific measurement. The constants may be determined based on, e.g., the acquired information and the physiological parameter of interest (e.g., the blood pressure), from the subject, or from other subjects (e.g., a sub-group of a general population). The sub-group may share a same or similar characteristic including, for example, age, gender, nation, stature, weight, a body fat percentage, color of skin, a family health history, a life style, an exercise habit or other habit, diet, occupation, illness history, education background, marital status, religious belief, or the like, or any combination thereof. The value of a and the value of b may be specified by a subject, a user other than the subject, the system 100, or the like.

In one example, the measured PTT is 1 second, and only one or more sets of calibration values (C) with a $PTT_0$ value falling within the range from 1-a second and 1+b second may be considered. The value of a and the value of b may be the same or different. Merely by a way of example, the value of a is factor1*PTT, the value of b is factor2*PTT. The factor1 and factor2 may be any number in the range of (0, 1). In some embodiments, factor1 or factor2 may be 2%, or 5%, or 8%, or 10%, or 12%, or 15%, or 20%, or 25%, or larger than 25%. In some embodiments, factor1 or factor2 may be lower than 50%, or lower than 40%, or lower than 30%, or lower than 25%, or lower than 20%, or lower than 15%, or lower than 12%, or lower than 10%, or lower than 8%, or lower than 5%. Factor1 and facor2 may be the same or different.

More descriptions regarding methods, models, calibration data for calculating and calibrating the physiological parameter of interest may be found in International Patent Application No. PCT/CN2015/083334 filed Jul. 3, 2015, which is hereby incorporated by reference.

While the foregoing has described what are considered to constitute the present disclosure and/or other examples, it is understood that various modifications may be made thereto and that the subject matter disclosed herein may be implemented in various forms and examples, and that the disclosure may be applied in numerous applications, only some of which have been described herein. Those skilled in the art will recognize that present disclosure are amenable to a variety of modifications and/or enhancements. For example, the pre-treatment step 720 may be unnecessary. Additionally, a third signal may be acquired if needed, and the third signal may be a signal with the same type with the first signal or the second signal, or may be a signal different with the first signal or the second signal.

FIG. 8-A through FIG. 8-E provide an exemplary signal processing according to some embodiments of the present disclosure. The one or more second signals mentioned in FIG. 7 may be analyzed and processed. The analysis and process may be performed by the analysis module 220. The signals (S) may be acquired in step 801. The acquisition may be performed by the information acquisition module 210. The signals (S) to be processed may be multiple PPG signals, multiple series of PPG signals, multiple blood oxygen data, multiple series of blood oxygen data, multiple body temperature data, multiple series of body temperature data, or the like, or a combination thereof. As used herein, a series of data refers to a group or a set of data detected from a specific body location of the subject. It is to say that multiple series of PPG signals refers to multiple group of PPG signals detected from multiple body locations of the subject.

Then whether to select one or more body locations where signals are to be acquired may be determined in step 802. If the answer is "yes", one or more body locations may be selected in step 807 and the signals detected from the selected body location(s) may be accessed or acquired in step 808. After the signals are accessed or acquired, at least some steps starting from node A 809 as illustrated in FIG. 8-B may be performed.

If no body locations are selected, a plurality of signals detected from multiple body locations may be loaded in step 803. The signals may be loaded from the information acquisition module 210, the server 120, the storage unit 480, a storage device anywhere disclosed in the present disclosure, or the like, or a combination thereof. In some embodiments, the signals may include multiple PPG signals detected by multiple sensors placed on multiple body locations. For example, multiple PPG signals may be detected by multiple sensors placed on the left arm, the right arm, the left leg, the right leg, or the like, or a combination thereof. In some embodiments, the signals may include multiple series of PPG signals detected by multiple sensor arrays placed on multiple body locations. For example, the signals may include a series of PPG signals detected by a sensor array placed on a body location and another series of PPG signals detected by another sensor array placed on another body location, or the like, or a combination thereof. Similarly, the signals may include blood oxygen data, body temperature data or other physiological data detected from multiple body locations, or the like, or a combination thereof. The multiple body locations may include the head, the neck, the chest, the abdomen, the upper arm, the wrist, the waist, the upper leg, the knee, the ankle, or the like, or a combination thereof.

At least some of the plurality of signals may be processed to provide a new signal in step 804. The new signal may be a signal derived from the plurality of signals loaded in step 803. The new signal may be selected from the plurality of signals loaded in step 803. The new signal may be a signal calculated based on the plurality of signals loaded in step 803. Methods of processing may include analog to digital conversion, digital to analog conversion, statistical analysis, least square method, method of mean value, modeling method, linear function method, history threshold iteration method, comparison method, inductive method, image method, or the like, or a combination thereof.

In some embodiments, the plurality of PPG signals may be multiple series of PPG signals. The multiple series of PPG signals may first be converted from analog signals to digital signals expressed as below.

$$S_n(t_i) \rightarrow D_n(t_i, A_i). \qquad \text{Equation 2}$$

As used herein, $S_n(t_i)$ refers to a PPG signal, $D_n(t_i, A_i)$ refers to the corresponding converted digital signal, $t_i$ refers to a time point, $A_i$ refers to the amplitude of the corresponding data point of the time point.

Then the data points corresponding to a time point may be performed by a mathematical operation (for example, an averaging operation), i.e., the amplitudes of the data points may be operated to a processed value. The mathematical operation process continues until the data points of all the time points are processed. After the process is finished, the processed values may be converted from digital data to an analog signal. Thus the initial multiple series of PPG signals are fused to a final new PPG signal.

In some embodiments, multiple blood oxygen data or multiple body temperature data may be acquired from multiple body locations of the subject. The multiple blood oxygen data may be processed (for example, averaged) to generate a new blood oxygen value. Similarly, the multiple body temperature data may be processed to generate a new body temperature value.

A physiological parameter of interest may be calculated based on the new signal in step 805. In some embodiments, the new signal may be a PPG signal. A blood pressure may be calculated based on the PPG signal and an ECG signal. The ECG signal may be acquired by the ECG acquisition unit 430. More descriptions regarding the method and process of the blood pressure calculation may be found in International Patent Application No. PCT/CN2015/083334 filed Jul. 3, 2015. The calculated physiological parameter of interest, the acquired signals (S), or physiological data of the subject may be uploaded to personal health manager 900 in step 806. The personal health manager 900 may be described in detail in FIG. 9.

FIG. 8-B illustrates the process starting from node A 809 regarding a signal processing of a body location according to some embodiments of the present disclosure. A body location of the subject may be determined in step 810. The body location may be the head, the neck, the chest, the abdomen, the upper arm, the wrist, the waist, the upper leg, the knee, the ankle, or the like, or a combination thereof. Signals detected from the determined body location may be loaded in step 811. For the determined body location, a series of signals may be acquired by a sensor array. After the body location is determined and the signals are loaded, a reference signal may be set in step 812. In some embodiments, the reference signal may be a real physiological signal, or may be a virtual simulated signal. In some embodiments, the reference signal may be an integral signal, or may be a portion of an integral signal. In some embodiments, the reference signal may be an analog signal, or may be a digital signal. In some embodiments, the reference signal may be a waveform, or may be one or more data points. In some embodiments, the reference signal may be an accurate signal waveform, or may be a schematic outline. In some embodiments, the reference signal may be an independent signal, or may be a data range. In some embodiments, the reference signal may be a time domain signal, or may be a frequency domain signal. In some embodiments, the reference signal may be a signal detected from the subject, or may be a signal detected from a subject of a peer group. As used herein, the peer group is defined as a group of people sharing at least some same or similar characteristics, for example, same gender, similar age, similar height, similar weight, similar arm length, similar illness history, or the like, or a combination thereof.

A comparison between the reference signal and the loaded signal(s) may be performed in step 813. The comparison may be with respect to the waveform of the reference signal and the waveform of the loaded signal(s). The comparison may be with respect to a feature of the reference signal and a corresponding feature point of the loaded signal(s). Exemplary features may include the peak, the valley, the time reaching the peak or valley, frequency, or the like, or a combination thereof. The comparison may provide a comparison result. The comparison result may be provided in the form of, for example, text, a graph, a three dimensional image, a code, a voice message, video, an audio alert, a haptic effect, or the like, or a combination thereof.

In step 814, a determination may be made as to whether the signals are satisfied a condition (for example, a condition relating to a threshold) based on the comparison result generated in step 813. The condition may be pre-determined or dynamically provided. In some embodiments, the condition may be constant or variable. For instance, the condition may be a predetermined profile as a function of, for example, the subject's age, gender, height, body weight, or the like, or a combination thereof. The determination may be made by the system or a portion thereof (for example, based on an instruction provided by a subject, a user other than the subject, a third party, or an instruction or a rule derived by machine learning of prior data, prior behaviors of the subject, or of a user other than the subject), or provided by the subject or by a user other than the subject, or by a third party related to the subject (for example, a doctor).

In step 814, the comparison result may be loaded and checked according to the condition. If the comparison result does not satisfy the condition, the corresponding acquired signal may be abandoned in step 815. Merely by way of example, in some embodiments, if the difference between the waveform of the acquired signal and the waveform of the reference signal does not satisfy a condition (for example, exceeds a threshold), the acquired signal may be abandoned. In some embodiments, compared with the reference signal, if a deviation of a data point of the acquired signal exceeds a threshold and therefore does not satisfy a condition, then the acquired signal may be abandoned. As used herein, a deviation may refer to the difference between the value of a data point of the acquired signal with that of the reference signal. In some embodiments, compared with the reference signal, if a feature of the acquired signal does not match a corresponding feature of the reference signal, the acquired signal may be determined to fail to satisfy a condition and may be abandoned. A signal(s) not abandoned based on, for example, the comparison, may be referred to as a reserved signal. The descriptions above are only provided for illustration purposes, and not intended to limit the scope of the present disclosure.

In step 816, a data type conversion may be performed on the reserved signals if needed. The data type conversion may be an analog to digital conversion. In some embodiments, the reserved signal may be expressed as S(t), the converted signal may be expressed as D(t, A). The data type conversion may be expressed as below.

$$S_1(t) \rightarrow D_1(t, A) = \{P_{11}(t_1, A_{11}), P_{12}(t_2, A_{12}), \ldots, P_{1m}(t_m, A_{1m}),\}$$
$$S_2(t) \rightarrow D_2(t, A) = \{P_{21}(t_1, A_{21}), P_{22}(t_2, A_{22}), \ldots, P_{2m}(t_m, A_{2m}),\}$$
$$\ldots$$
$$S_n(t) \rightarrow D_n(t, A) = \{P_{n1}(t_1, A_{n1}), P_{n2}(t_2, A_{n2}), \ldots, P_{nm}(t_m, A_{nm}),\}$$

Equation 3

As used herein, the factor t may refer to a time point, the factor P may refer to the data point of the signal at the time point t, the factor A may refer to the amplitude of the signal at the time point t. In some embodiments, if the reserved signal is a PPG signal, an analog to digital conversion may be performed. In some embodiments, if the reserved signal is a body temperature signal or a blood oxygen signal, then there is no need to perform a data type conversion on the reserved signals. Using the PPG signal as an example, after the data type conversion is performed, a PPG signal may be converted from a waveform signal to a series of data points. Then it may follow at least some steps starting from node B 817 as illustrated in FIG. 8-C.

FIG. 8-C illustrates the process starting from node B 817 regarding a signal process according to some embodiments of the present disclosure. In step 818, a series of data points expressed as a set D may be acquired from an analog signal by a data type conversion in step 816. In step 819, a time point may be selected from a time point set T. The set D and the set T may be expressed as below.

$$D = \begin{Bmatrix} \{P_{11}(t_1, A_{11}), P_{12}(t_2, A_{12}), \ldots, P_{1m}(t_m, A_{1m}),\} \\ \{P_{21}(t_1, A_{21}), P_{22}(t_2, A_{22}), \ldots, P_{2m}(t_m, A_{2m}),\} \\ \ldots \\ \{P_{n1}(t_1, A_{n1}), P_{n2}(t_2, A_{n2}), \ldots, P_{nm}(t_m, A_{nm}),\} \end{Bmatrix},$$ Equation 4

$$T = \{t_1, t_2, \ldots, t_m\}.$$ Equation 5

Then a data distribution of the corresponding series of data points may be analyzed in step 820. Merely by way of example, if the time point $t_1$ is selected, a distribution of the corresponding series of data points $\{P_{11}(t_1,A_{11}), P_{21}(t_1, A_{21}), \ldots, Pn_1(t_1,An_1)\}$ may be analyzed in step 820. The analysis may be a statistical analysis, a mathematical calculation, a regression analysis, a cluster analysis, an analysis of variance, or the like, or a combination thereof. After the data distribution analysis, a statistical result of the distribution of the data points may be generated. The statistical result may be a table format including a series of data extent and corresponding percentage. The statistical result may be a data scatter plot (for example, a histogram, a pie, a star chart, or the like). The statistical result may be a mathematical expression. The statistical result may be a mathematical model. The description above are only provided for illustration purposes, and not intended to limit the scope of the present disclosure. The statistical result also may be exhibited in other forms.

Then a threshold may be set in step 821. The threshold may be a percentage, an absolute value, a value range, or the like, or a combination thereof. In some embodiments, the threshold value expressed as v may be selected from an interval a<v<b. In some embodiments, the threshold may be a value range expressed as a<v<b. The constants a and b may be determined for a specific analysis. In some embodiments, the constants may be a default value determined by the system or set by, for example, a subject, a user other than the subject, a third party, or the like, or a combination thereof. In some embodiments, the constants may be determined based on the acquired information and the physiological parameter of interest (for example, the blood pressure) to be calculated, from the subject, or from other subjects (for example, a sub-group of a general population). The sub-group may share a same or similar characteristic including, for example, age, gender, nation, stature, weight, a body fat percentage, color of skin, a family health history, a life style, an exercise habit or other habit, diet, occupation, illness history, education background, marital status, religious belief, or the like, or any combination thereof. In some embodiments, the constants may be set by the subject, a user other than the subject, a related third party (for example, a doctor), or the like.

In step 822, a comparison may be performed to determine whether the data point exceeds the threshold regarding the distribution of the data points. If the answer is "yes," the corresponding data point may be abandoned in step 823. Then the reserved data points may be performed by a mathematical operation in step 824. The mathematical operation may be, for example, a direct primary calculation including four rules of arithmetic, a power operation, a rooting operation, or the like, or a combination thereof. The mathematical operation may be, for example, a functional operation including a linear function, a quadratic function, a high order function, a polynomial, or the like, or a combination thereof. The mathematical operation may be, for example, a simulation operation including a physical simulation, a mathematical simulation, a semi-physical simulation, or the like, or a combination thereof. The descriptions above are only provides for illustration purposes, and not intended to limit the scope of present disclosure. Merely by way of example, the reserved data points may be performed by an averaging operation which may be expressed as below.

$$\text{AVERAGE}\{P_{11}(t_1,A_{11}), P_{21}(t_1,A_{21}), \ldots, P_{n1}(t_1,A_{n1})\}.$$ Equation 6

After the mathematical operation, the system may proceed to step 819 to select another time point and perform another data processing starting from step 820 until all the time points are selected and all the corresponding data points are analyzed and processed. In step 825, the processed data may be performed by an inverse data type conversion if a data type conversion was performed in step 816. Then a new signal based on the results of the above steps may be generated in step 826. Then it may follow at least some steps starting from node C 827 as illustrated in FIG. 8-D.

FIG. 8-D illustrates the process starting from node C 827 regarding a signal process according to some embodiments of the present disclosure. Through the steps of processing starting from node B 817, a new signal may be generated in step 826. A physiological parameter of interest may be calculated based on the new signal in step 828. In some embodiments, the new signal may be a PPG signal. A blood pressure may be calculated based on the PPG signal and an ECG signal. The ECG signal may be acquired by the ECG acquisition unit 430 and stored in the storage unit 480 or the server 120 or a storage device disclosed anywhere in the present disclosure. PTT may be determined based on the ECG signal and the PPG signal. During the calculation of the physiological parameter of interest, a calibration process (not shown in FIG. 8-D) may be performed. More descriptions regarding the method and process of the calculation and the calibration may be found in International Patent Application PCT/CN2015/083334 filed Jul. 3, 2015, the entire contents of which are hereby incorporated by reference.

After the physiological parameter of interest is calculated, then whether to perform a comparison with data of other body locations may be chosen in step 829. The determination may be made by the system or a portion thereof (for example, based on an instruction provided by a subject, a user other than the subject, a third party, or an instruction or a rule derived by machine learning of prior data, prior behaviors of the subject, or of a user other than the subject), or provided by the subject or by a user other than the subject. If the comparison is chosen, it may follow at least some steps starting from node D 830 as illustrated in FIG. 8-E.

If the comparison is not chosen, whether to perform a comparison with historical data may be determined in step 831. The determination may be made by the system or a portion thereof (for example, based on an instruction provided by a subject, a user other than the subject, or an instruction or a rule derived by machine learning of prior data, prior behaviors of the subject, or of a user other than the subject), or provided by the subject or by a user other than the subject. In some embodiments, a variation from historical data may be calculated in step 832 if the comparison determination is made. As used herein, the variation may be determined based on a comparison between the calculated physiological parameter of interest and a historical data. The historical data may be a physiological parameter of interest estimated or measured before a time interval ago. The time interval may be an hour, a day, a week, a month, a year, or the like, or a combination thereof. In some embodiments, a variation curve compared with historical data may be generated in step 832. As used herein, the variation curve may be a curve representing the physiological parameter changing with time within a time interval. Similarly, the time interval may be an hour, a day, a week, a month, a year, or the like, or a combination thereof. The variation or the variation curve may be stored in the analysis module 220 or the server 120 or personal health manager 900. A threshold for a physiological parameter of interest may be set in step 834. The threshold may be set by the subject, a user than the subject, a third party (for example, a doctor), the system default, or the like, or a combination thereof. The threshold may be an absolute value, a value range, a variation value between the current physiological parameter of interest with one or more historical data, or the like, or a combination thereof. The threshold may be set based on the basic information of the subject including age, gender, height, weight, illness history, or the like, or a combination thereof. The threshold may be set based on historical data of the subject. The threshold may be set based on the statistical data of a peer group. The threshold may be set based on empirical data of a group not limited to a peer group. Merely by way of example, a threshold for a blood pressure may set as below.

$$DBP \epsilon \{DBP_a, DBP_b\}, SBP \epsilon \{SBP_a, SBP_b\}. \quad \text{Equation 7}$$

For instance, for an ordinary person with normal blood pressure, the normal DBP may be ≈120 mmHg (recorded as $DBP_N$), the normal SBP may be ≈80 mmHg (recorded as $SBP_N$). The threshold $DBP_a$, $DBP_b$, $SBP_a$ and $SBP_b$ may be set as a certain percentage of the normal value. For example, $DBP_a$ may be set as 90% $DBP_N$ and $DBP_b$ may be set as 110% $DBP_N$. Similarly, $SBP_a$ and $SBP_b$ may be set as 90% $SBP_N$ and 110% $SBP_N$, respectively. According to some embodiments of the present disclosure, the values of $DBP_a$, $DBP_b$, $SBP_a$ and $SBP_b$ may be personalized. And the values may vary under different situations (for example, when the subject is exercising or asleep, at different times of a day, at the same or similar time on different days, or the like, or a combination thereof.)

In step 834, a comparison between the physiological parameter of interest with the threshold may be performed. If the value of the physiological parameter exceeds the threshold, or if the variation calculated in step 832 exceeds the threshold, an alert may be generated in step 835. The alert may include information relating to the subject, the threshold, the event that has triggered the alert, the time when the event occurred, relevant historic information (for example, the frequency that similar events have occurred, the occurrence of similar events within a time period, etc.), the environmental information, or some other related information. The information related to the subject may include the value of the physiological parameter of interest, or the variation or the variation curve generated in step 832. Then the alert may be transferred to a related third party in step 836. The related third party may be a doctor, a healthcare worker, a medical institution, a research facility, a peripheral device of the subject or a user well-connected to the subject, or the like. If the value of the physiological parameter is within the scope of the threshold value, or if the variation calculated in step 832 is within the scope of the threshold value, the results may be uploaded to personal health manager in step 837. And then the system may return to the steps starting from node A 809 to determine another body location and perform the subsequent signal/data processing.

FIG. 8-E illustrates the subsequent steps regarding a process and an analysis of the calculated physiological parameters of interest of multiple body locations from node D 830 according to some embodiments of the present disclosure. The physiological parameters of interest of multiple body locations may be loaded in step 838. The physiological parameters of interest may be loaded from the analysis module 220, the server 120, any storage device disclosed anywhere in the present disclosure, or the like, or a combination thereof. In some embodiments, the physiological parameter of interest may be the blood pressure of the subject. A relation information among the physiological parameters of interest of multiple body locations may be generated in step 839. In some embodiments, a relation information among the second signals or relation information among the plurality of parameters determined in step 750 (e.g., PTT) may be generated. The form of the relation information may be text, a graph, a three dimensional image, a code, a voice message, video, an audio alert, a haptic effect, or the like, or a combination thereof. Merely by way of example, the relation information may be in the form of a curve, a histogram diagram, a data distribution of different body locations, a difference value between the calculated physiological parameters with a reference value (for example, the reference value being a physiological parameter of an ordinary person), information based on a comparison between the left side and the right of the body, a difference between a calculated physiological parameter of one body location with that of another body location (for example, the blood pressure value of the arm and the blood pressure value of the leg) of a subject, or the like, or a combination thereof.

In step 840, the system may detect whether errors occur. The error may be an abnormal value, an abnormal wave form or an abnormal change thereof, an asymmetry information between the left side and the right side of the body of a subject, a deviation from a reference value, or the like, or a combination thereof. If errors are detected, the corresponding data point and/or the associated body location (for example, the body location where the data point was acquired) may be marked in step 843. Then it may proceed to node A 809 and follow at least some of the steps starting from node A 809 as illustrated in FIG. 8-B and the description thereof. That is, a new acquisition process and analysis process regarding the marked body location may be performed.

If no errors are detected, the relation information may be analyzed in step 841. In some embodiments, the analysis may be a comparison with historical data for generating a variation result. In some embodiments, the analysis may be a statistical analysis for generating a statistical result regarding a comparison with data of a peer group (for example, a group of people sharing same age and same gender, or the like) In some embodiments, the analysis may be a mathematical operation for generating a three dimensional display of the relation information. After the relation information is analyzed, a guide information may be generated based on the analysis.

In some embodiments, the guide information may be a prompting message regarding selection of calculation models which may be used to calculate the physiological parameter of interest of the subject (more descriptions regarding the calculation models may be found in International Patent Application No. PCT/CN2015/083334 filed Jul. 3, 2015, the contents of which are hereby incorporated by reference). Merely by way of example, the relation information generated in step 839 may be a distribution of blood pressure values of multiple body locations of the subject. For another example, the relation information generated in step 839 may be an interrelation of the determined plurality of parameters (e.g., PTTs) or the acquired plurality of second signals. In some embodiments, guide information based on the distribution of blood pressure values of multiple body locations may be provided to the system. Then the system may select a favorite model or a proper model for a specific subject to calculate blood pressure during a next calculation process. For example, blood pressure distributions of different subjects may be different, or blood pressure distributions of a specific subject may be different under different situations (e.g., the blood pressure distribution may vary with environment temperature, air humidity, or the like). The selection of calculation models may be performed based on an analysis result of historical data, or may be performed based on a preset condition (e.g., different blood pressure distributions may correspond to different calculation models). In some embodiments, guide information based on the interrelation of the determined plurality of parameters or the acquired plurality of second signals may be provided to the system. Then the system may select a favorite model or a proper model for a specific subject to calculate blood pressure before a calculation process.

In some embodiments, the guide information may be a modified model used for calculating the physiological parameter of interest of the subject. Merely by way of example, an initial model used for calculating blood pressure of body location 1 may be expressed in Equation 8 according to the description in the International Patent Application No. PCT/CN2015/083334 filed Jul. 3, 2015, the contents of which are hereby incorporated by reference.

$$BP_1 = f(PTT_1), \quad \text{Equation 8}$$

In some embodiments. while the relation information of the blood pressure value of the body location 1 with that of one or more other body locations is analyzed (for example, the relation information between the blood pressure value of the arm and that of the leg, or the relation information among the blood pressure value of the head and those of the arm, the leg, the wrist, or the like), a compensation term may be generated based on the analysis result. The compensation term may be a function of the relation information. The function form may be based on a feature of the subject (for example, height, weight, gender, historical data, etc.). The compensation term may be added to the initial model to generate a modified model in Equation 9. The guide information regarding a modified calculation model may increase the calculation accuracy.

$$BP_1 = f(PTT_1) + f_{compensation}, \quad \text{Equation 9}$$

In some embodiments, while the relation information among the determined plurality of parameters or the acquired plurality of second signals may be analyzed, a compensation term may be generated based on the analysis.

In some embodiments, the guide information may be a push information regarding daily activities. Exemplary information may include dietetic varieties, water intake, sugar intake, sleep time, work and rest, duration and type of exercise, exercise intensity, or the like, or a combination thereof. In some embodiments, the guide information may be an information for reference provided to a related third party (for example, a doctor, a healthcare worker, a medical institution, a research facility, or the like, or a combination thereof). For example, the blood related information of different body locations of the subject may be considered as a guide or a reference for a blood related surgery (for example, the determination of the surgery spot, or whether needs anesthesia, or the like). For another example, the physiological parameters of different body locations of the subject may be considered as a guide or a reference for a medicine treatment (for example, type and dose of the drugs, medication time, oral or injectable, or the like). The guide information may be uploaded to the personal health manager 900 in step 844. The person health manager 900 may push the guide information to, for example, the subject, a user other than the subject, a third party, or the like, or a combination thereof. The guide information may be viewed by, for example, the subject, a user other than the subject, a third party, or the like, or a combination thereof. The guide information may be accessible from, for example, a user interface provided by the system.

Figure 9:
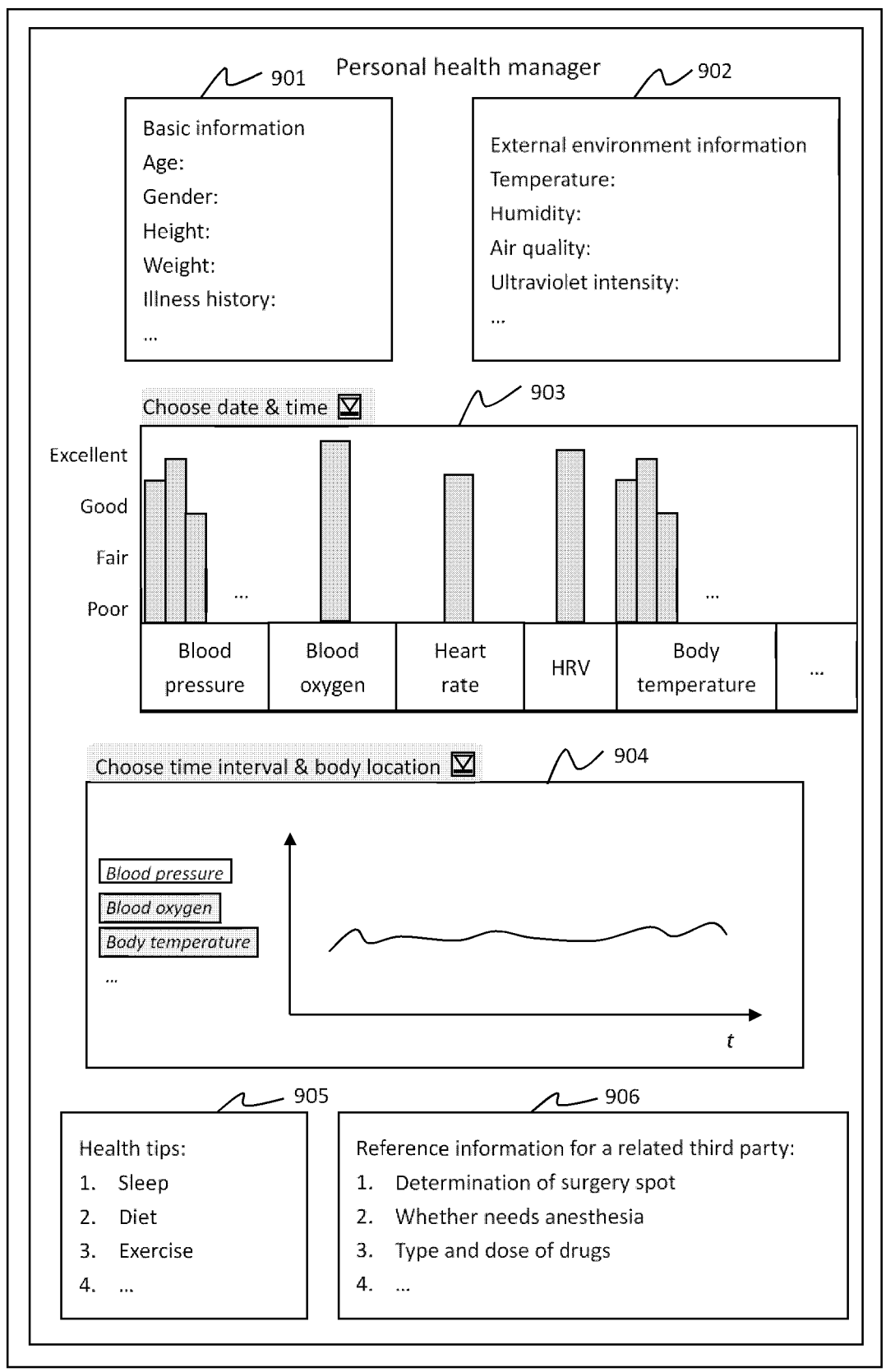
FIG. 9 illustrates an exemplary personal health manager according to some embodiments of the present disclosure.

FIG. 9 is an example of the composition and organization of the personal health manager 900 according to some embodiments of the present disclosure. The personal health manager 900 may be stored in the server 120, locally on a measuring device 110, a terminal 140 connected or communicated with the system, or the like, or a combination thereof. For instance, the personal health manager 900 may be stored in a device of a third party. The personal health manager 900 may be displayed on a terminal 140, a display device of the system (not shown), a display device of a third party, or the like, or a combination thereof. The personal health manager 900 may have different sections including basic information 901, external environmental information 902, the status or of the physiological parameters of interest of different body locations 903, variations of physiological parameters of interest with time 904, health tips 905, reference information provided for a related third party 906, or other related sections.

The basic information 901 may include age, gender, height, weight, illness history, or the like, or a combination thereof. The external environmental information 902 may include temperature, humidity, air quality, ultraviolet intensity, or the like, or a combination thereof. The basic information and the external environmental information may be acquired by the information acquisition module 210. The information may be updated at a certain frequency (for example, once an hour, once a day, twice an hour, twice a day, three times an hour, three times a day, or the like). The information may be displayed selectively based on an option or an instruction of the subject, or may be based on the system default.

A status of a physiological parameter of interest may be displayed in the section 903. The physiological parameter of interest may include blood pressure, blood oxygen, heart rate, HRV, body temperature, or the like, or a combination thereof. The subject, a user other than the subject, or a related third party may choose date and time to review the status of the physiological parameters. The status level may include excellent, good, fair and poor. The different rectangular columns represent different locations including the head, the neck, the chest, the abdomen, the upper arm, the wrist, the waist, the upper leg, the knee, the ankle, or the like, or a combination thereof. Through the section 903, the status of the physiological parameters of interest of the subject on different body locations may be displayed vividly in real time. And also historical information may be displayed based on an option of the subject regarding date and time.

A variation of a physiological parameter of interest may be displayed in section 904. The subject, a user other than the subject, or a related third party may choose a time interval and a body location, then the variations of the physiological parameters of interest may be displayed (as is symbolically illustrated in FIG. 9). The time interval may be an hour, a day, a week, a month, two months, or the like, or a combination thereof. The subject, a user other than the subject, or a related third party may click the icons to see the variation curves of different physiological parameters of interest. The health tips section 905 may include information regarding sleep, diet, exercises, or the like, or a combination thereof. The health tips may be retrieved from the server 120 based on the basic information of the subject, the calculated physiological parameters of interest, the variations, or the like, or a combination thereof. A related third party (for example, a doctor, a healthcare worker, a medical institution, a research facility, a peripheral device of the subject or a user well-connected to the subject, or the like) may input some health tips in the section 905. Similarly, the subject or a user other than the subject also may input a memo list regarding sleep, diet, exercises, or the like. The subject may customize an information push regarding health tips based on an option or an instruction.

Reference information for a related third party may be displayed in section 906. The related third party may be a doctor, a healthcare worker, a medical institution, a research facility, or the like, or a combination thereof. The reference information may be generated based on the status of the calculated physiological parameters of interest, the basic information of the subject, or both. The reference information may include information regarding determination of surgery spot, or whether needs anesthesia, or type and dose of drugs, or the like, or a combination thereof. The reference information may provide some guidance to the related third party at a right moment.

Figure 10:
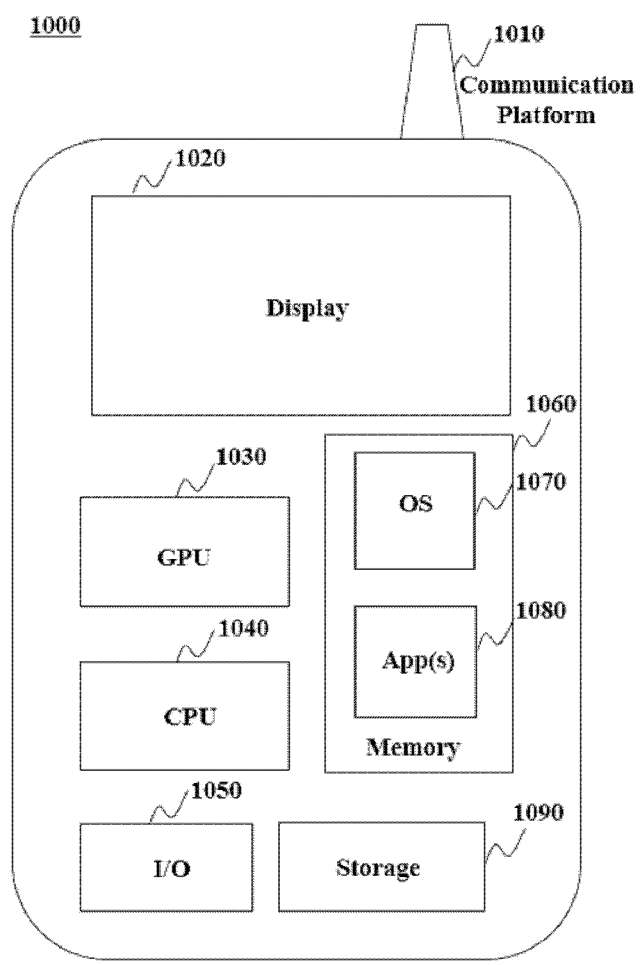
FIG. 10 depicts the architecture of a mobile device that may be used to implement a specialized system or a part thereof incorporating the present disclosure.

FIG. 10 depicts the architecture of a mobile device that may be used to realize a specialized system implementing the present disclosure. In this example, the device (for example, the terminal 140) on which information relating to blood pressure monitoring is presented and interacted-with is a mobile device 1000, including, but is not limited to, a smart phone, a tablet, a music player, a handled gaming console, a global positioning system (GPS) receiver, and a wearable computing device (for example, eyeglasses, wrist watch, etc.), or in any other form factor. The mobile device 1000 in this example includes one or more central processing units (CPUs) 1040, one or more graphic processing units (GPUs) 1030, a display 1020, a memory 1060, a communication platform 1010, such as a wireless communication module, storage 1090, and one or more input/output (I/O) devices 1050. Any other suitable component, including a system bus or a controller (not shown), may also be included in the mobile device 1000. As shown in FIG. 10, a mobile operating system 1070, for example, iOS, Android, Windows Phone, etc., and one or more applications 1080 may be loaded into the memory 1060 from the storage 1090 in order to be executed by the CPU 1040. The applications 1080 may include a browser or any other suitable mobile apps for receiving and rendering information relating to blood pressure monitoring or other information from the engine 200 on the mobile device 1000. User interactions with the information stream may be achieved via the I/O devices 1050 and provided to the engine 200 and/or other components of system 100, for example, via the network 150.

To implement various modules, units, and their functionalities described in the present disclosure, computer hardware platforms may be used as the hardware platform(s) for one or more of the elements described herein (for example, the engine 200, and/or other components of the system 100 described with respect to FIGS. 1-9 and 12). The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 11:
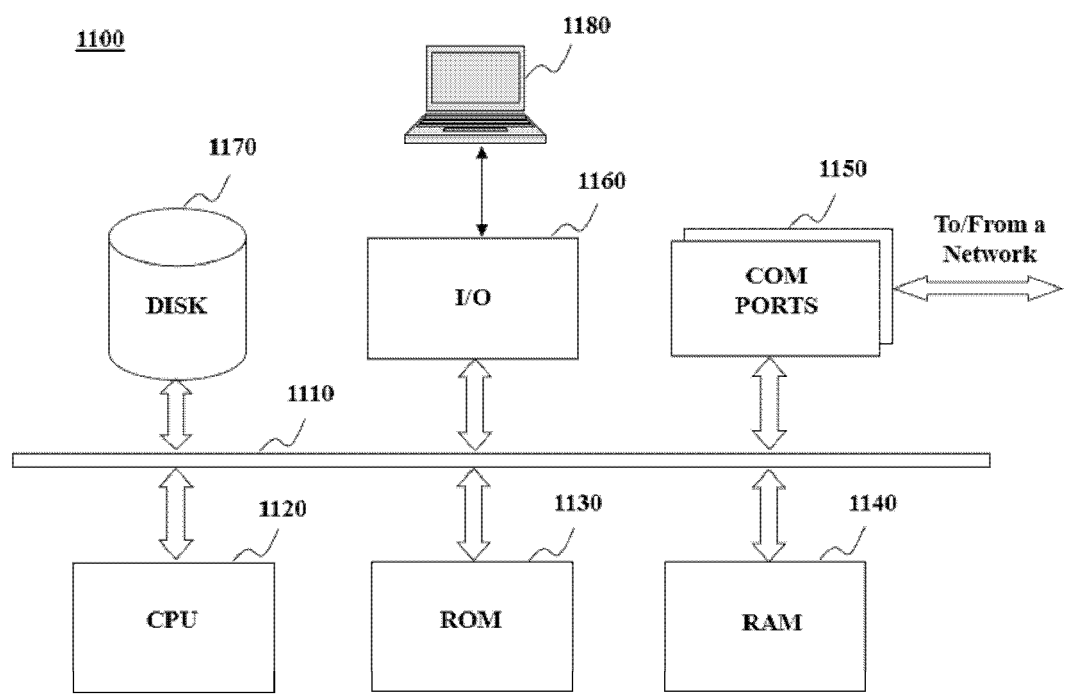
FIG. 11 depicts the architecture of a computer that may be used to implement a specialized system or a part thereof incorporating the present disclosure.

FIG. 11 depicts the architecture of a computing device that may be used to realize a specialized system implementing the present disclosure. Such a specialized system incorporating the present teaching has a functional block diagram illustration of a hardware platform that includes user interface elements. The computer may be a general purpose computer or a special purpose computer. Both may be used to implement a specialized system for the present disclosure. This computer 1100 may be used to implement any component of the blood pressure monitoring as described herein. For example, the engine 200, etc., may be implemented on a computer such as computer 1100, via its hardware, software program, firmware, or a combination thereof. Although only one such computer is shown, for convenience, the computer functions relating to the blood pressure monitoring as described herein may be implemented in a distributed fashion on a number of similar platforms, to distribute the processing load.

The computer 1100, for example, includes COM ports 1150 connected to and from a network connected thereto to facilitate data communications. The computer 1100 also includes a central processing unit (CPU) 1120, in the form of one or more processors, for executing program instructions. The exemplary computer platform includes an internal communication bus 1110, program storage and data storage of different forms, for example, disk 1170, read only memory (ROM) 1130, or random access memory (RAM) 1140, for various data files to be processed and/or transmitted by the computer, as well as possibly program instructions to be executed by the CPU. The computer 1100 also includes an I/O component 1160, supporting input/output between the computer and other components therein such as user interface elements 1180. The computer 1100 may also receive programming and data via network communications.

Hence, aspects of the methods of the blood pressure monitoring and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors, or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of the engine 200 into the hardware platform(s) of a computing environment or other system implementing a computing environment or similar functionalities in connection with the blood pressure monitoring. Thus, another type of media that may bear the software elements includes optical, electrical and electromagnetic waves, such as used across physical interfaces between local devices, through wired and optical land line networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present disclosure are amenable to a variety of modifications and/or enhancements. For example, although the implementation of various components described above may be embodied in a hardware device, it may also be implemented as a software only solution—for example, an installation on an existing server. In addition, the blood pressure monitoring system as disclosed herein may be implemented as a firmware, firmware/software combination, firmware/hardware combination, or a hardware/firmware/software combination.

EXAMPLE

The following example is provided for illustration purposes, and not intended to limit the scope of the present disclosure.

Figure 12:
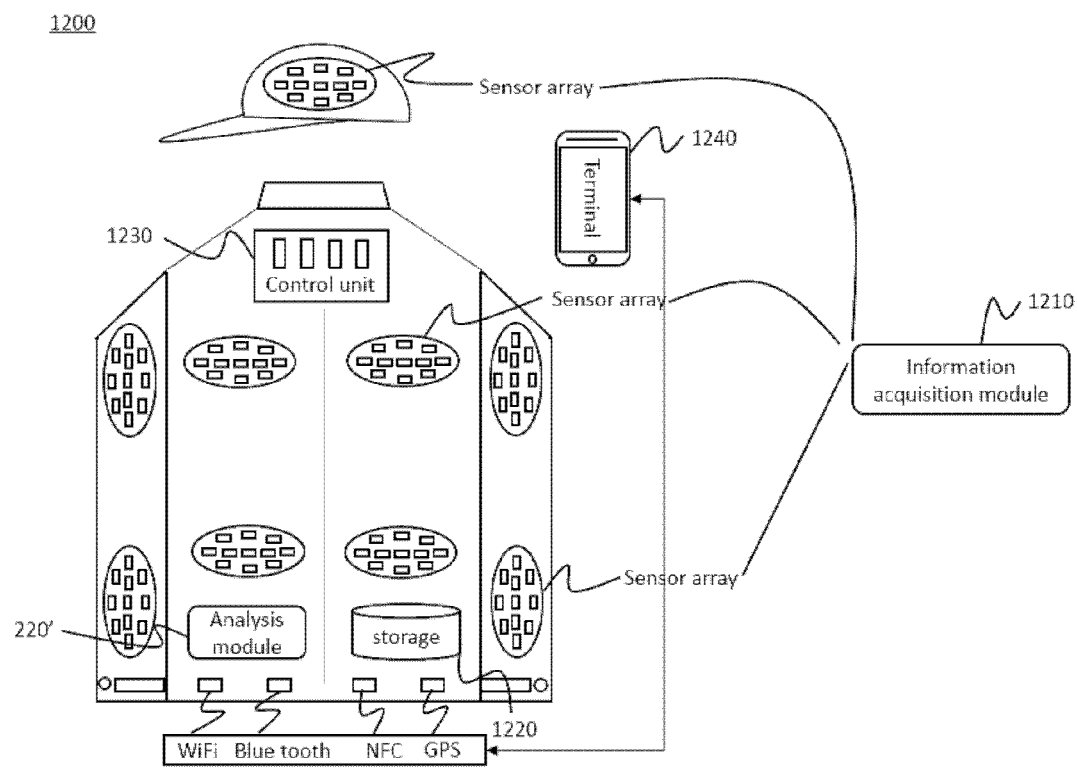
FIG. 12 illustrates an exemplary device according to some embodiments of the present disclosure.

A system used for measuring blood pressure may include a testing device 1200, peripheral equipment 240 and a server 120. FIG. 12 illustrates an exemplary testing device according to some embodiments of the embodiment. The testing device 1200 may include an information acquisition module 1210, an analysis module 220', a storage 1220, and a control unit 1230. The testing device 1200 may be connected or otherwise communicate with a terminal 1240. The information acquisition module 1210 may include multiple sensor arrays arranged on multiple locations of the testing device 1200.

According to the embodiment, the information acquisition module 1210 is configured for acquiring information, for example, an ECG signal, a PPG signal, or the like, or a combination thereof. The analysis module 220' is configured for analyzing and processing the acquired information, or determining or estimating a physiological parameter (for example, the physiological parameter of interest), or both. The storage 1220 is configured for storing the detected or acquired signal, the physiological parameter, or the like, or a combination thereof. The control unit 1230 is configured for controlling the ON/OFF of the sensor arrays, the location of the sensor arrays, the arrangement of the sensor arrays, the information acquisition parameter configuration, or the like, or a combination thereof. In the embodiment, the control unit 1230 may be a stepper machine, or may be a micro-motor. According to the embodiment, the information acquisition module 1210 includes two acquisition units (not shown in FIG. 12), an ECG acquisition unit and a PPG acquisition unit. The ECG acquisition unit is configured for detecting an ECG signal. The PPG acquisition unit is configured for detecting a PPG signal. The acquired ECG signal and the PPG signal may be stored in the storage 1220, or in the server 120, or in the terminal 1240, or the like, or a combination thereof.

The testing device 1200 may be a wearable device or may be a portable device. The testing device 1200 may be a coat-like device. A schematic diagram of the coat-like device is illustrated in FIG. 12 (some details have been elided for brevity). It may be seen that multiple sensor arrays configured for detecting PPG signals are integrated into the coat. The sensor array may include multiple photoelectric sensors, or may include multiple receiving ends. One or more light sources (not shown in FIG. 12) may be integrated into the sensor array, or may be placed in other devices, or may be arranged in the testing device 1200 independently. The sensor array may be placed on the head, the chest, the upper arm, the wrist, or the like, or a combination thereof. The sensor array may be an oval array, a rectangular array, a rhombus array, a circular array, or the like, or a combination thereof. In the embodiment, the sensor array is an oval array. The arrangement of the photoelectric sensors within the sensor array shown in FIG. 12 is only provides for illustration purposes, the amount and the arrangement of the sensors may be adjusted under different situations. Merely by way of example, the number and the arrangement of the sensors may be customized based on the subject's requirements. In one example, if the subject wants to obtain a physiological information regarding an organ, the sensor array may be placed on a body location nearby the organ area. In another example, the arrangement of the sensors may be adjusted according the subject's body size. In another example, a memory metal may be used for remembering the location and the arrangement of the sensor array to achieve personalization purpose.

Although not shown in FIG. 12, an ECG acquisition unit configured for detecting ECG signals is integrated into the coat. The ECG acquisition unit includes 10 electrodes (four placed on the chest, two placed on the two arms, two placed on the two legs). The 10 electrodes may constitute 12 leads and an ECG signal may be detected. The detected ECG signals may be stored in the storage 1220, or may be stored in the server 120, or may be loaded by the analysis module 220' for subsequent calculation.

The coat may also include some other additional components including a WIFI device, a blue tooth device, a NFC device, a GPS device, or the like, or a combination thereof. For instance, the WIFI device may be used for linking to a wireless network. The blue tooth device may be used for data transformation among some wired or wireless terminals within a certain distance. The NFC device may be used to enable terminals establishing radio communication within a short distance (10 cm or less). The GPS device may allow the subject to find his own position, or the GPS device may be used to navigate, or the like, or a combination thereof. The additional components may be connected or otherwise communicate with the information acquisition module 210, the analysis module 220', the control unit 1230, the terminal 1240, and the server 120.

The coat may communicate with a healthcare provider located in a location remote from the subject. The communication may be achieved directly by the coat, or indirectly via, for example, the terminal 1240 carried by the subject. The physiological parameter, as well as location information, of the subject may be transmitted to the healthcare provider in real-time, periodically, or when a triggering event occurs. Exemplary trigger events are described elsewhere in the present disclosure. When an emergency occurs, for example, the physiological parameter exceeding a threshold, the healthcare provider may be notified, the subject may be located based on the positioning information from the GPS or location sensor, and medical services may be provided accordingly.

The analysis module 220' is configured for analyzing and processing a detected ECG signal, or multiple series of PPG signals detected by multiple sensor arrays, or the like, or a combination thereof. According to the embodiment, a series of PPG signals may be analyzed and processed. According to the embodiment, the sensor arrays may be placed on the chest, the abdomen, the upper arm, the wrist, the head, or the like. The sensor may include a series of photoelectric sensors arranged in an array (for example, an oval array, a rectangular array, or the like). Take the sensor array placed on the head for example, a series of PPG signals may be detected by the sensor array arranged in an oval array. The sensor array includes eleven (or more in other different situations) photoelectric sensors. Then eleven PPG signals may be detected by the eleven sensors. The eleven PPG signals may be analyzed and processed by the analysis module 220'. The eleven PPG signals may be compared with a reference signal to screen out and abandon signal(s) not satisfied the threshold condition. Then a data type conversion may be performed on the reserved PPG signals. If no signals are abandoned, then eleven analog PPG signals are converted to eleven series of data points. Furthermore, a time point corresponds to eleven data points as expressed below.

$$t_1: \begin{bmatrix} P_{1,1} \\ P_{1,2} \\ \ldots \\ P_{1,11} \end{bmatrix}, t_2: \begin{bmatrix} P_{2,1} \\ P_{2,2} \\ \ldots \\ P_{2,11} \end{bmatrix}, \ldots, t_n: \begin{bmatrix} P_{n,1} \\ P_{n,2} \\ \ldots \\ P_{n,11} \end{bmatrix}. \quad \text{Equation 10}$$

The eleven data points corresponding to a time point may be performed by a mathematical operation (for example, averaging) to generate a final data point. The final data points together with the time points may be performed by an inverse data type conversion. A new PPG signal may be generated. The new generated PPG signal together with the detected or acquired ECG signal may be used for calculating a physiological parameter of interest (for example, blood pressure).

The analysis may also may include pre-treatment, feature identification, parameter estimation, calibration, or the like, or a combination thereof. More descriptions regarding the analysis may be found in International Patent Application No. PCT/CN2015/083334 filed Jul. 3, 2015. The calculated physiological parameter of interest may be uploaded to personal health manager 900 in the server 120. The details may be displayed in the terminal 1240, or may be transmitted to a related third party (for example, a medical institution).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure. In addition, the term "logic" is representative of hardware, firmware, software (or any combination thereof) to perform one or more functions. For instance, examples of "hardware" include, but are not limited to, an integrated circuit, a finite state machine, or even combinatorial logic. The integrated circuit may take the form of a processor such as a microprocessor, an application specific integrated circuit, a digital signal processor, a micro-controller, or the like.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "circuit," "unit," "module," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—for example, an installation on an existing server or mobile device. In addition, the financial management system disclosed herein may be implemented as a firmware, firmware/software combination, firmware/hardware combination, or a hardware/firmware/software combination.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

We claim:

1. A device comprising:
   non-transitory computer readable memory storing instructions; and
   at least one processor that executes the instructions to perform operations comprising:
   receiving a first signal representing heart activity of a subject;
   receiving a plurality of second signals representing time-varying information on at least one pulse wave of the subject;
   identifying a first feature in the first signal;
   identifying, for each of the plurality of second signals, a second feature;
   computing a pulse transit time based on a difference between the first feature and at least one of the second features; and
   calculating a blood pressure of the subject according to a model based on the computed pulse transit time, the model comprising a compensation term relating to distribution or interrelation of the plurality of second signals or the second features thereof.

2. The device of claim 1, the operations further comprising selecting the model based on the plurality of the second signals or the second features thereof.

3. The device of claim 1, the receiving the first signal comprising communicating with a first sensor configured to acquire the first signal at a first location on the body of the subject.

4. The device of claim 1, the receiving the plurality of second signals comprising communicating with a plurality of second sensors configured to acquire the plurality of second signals at a plurality of second locations on the body of the subject.

5. The device of claim 4, at least one of the plurality of second sensors comprising a sensor array including a plurality of sensors, a plurality of receiving ends of one or more sensors, or a plurality of emitting ends of one or more sensors.

6. The device of claim 5, the sensor array having a configuration of an oval array, a rectangular array, a circular array, or a triangular array.

7. The device of claim 4, the plurality of second locations comprising at least one location selected from the head, the neck, the chest, the abdomen, the upper arm, the wrist, the waist, the upper leg, the knee, or the ankle of the subject.

8. The device of claim 4, the operations further comprising:
   calculating a plurality of blood pressures of the plurality of second locations on the body of the subject.

9. The device of claim 8, the operations further comprising:
   providing, based on the plurality of calculated blood pressures, a recommendation relating to the subject.

10. The device of claim 1, at least one of the first signal or the plurality of second signals comprising an optical signal or an electrical signal.

11. The device of claim 1, the operations further comprising receiving a set of calibration values, and
    the calculating the blood pressure comprising using the set of calibration values.

12. The device of claim 1, at least one of the first signal or the plurality of second signals comprising a PPG waveform, an ECG waveform, or a BCG waveform.

13. The device of claim 1, wherein
    the first feature of the first signal corresponds to a first time point; and
    the identifying, for each of the plurality of second signals, the second feature comprises:
    selecting a segment of each of the second signals, the segment occurring within a time window from the first time point; and
    locating the second feature corresponding to a second time point in the segment.

14. A method comprising:
    receiving a first signal representing a heart activity of a subject;
    receiving a plurality of second signals representing time-varying information on at least one pulse wave of the subject;
    identifying a first feature in the first signal;
    identifying, for each of the plurality of second signals, a second feature;

computing a pulse transit time based on a difference between the first feature and at least one of the second features; and calculating a blood pressure of the subject according to a model based on the computed pulse transit time, the model comprising a compensation term relating to distribution or interrelation of the plurality of second signals or the second features thereof.

15. The method of claim 14, further comprising acquiring the first signal at a first location on the body of the subject.

16. The method of claim 14, further comprising acquiring the plurality of second signals at a plurality of second locations on the body of the subject.

17. The method of claim 16, the plurality of second locations comprising at least one location selected from the head, the neck, the chest, the abdomen, the upper arm, the wrist, the waist, the upper leg, the knee, or the ankle of the subject.

18. The method of claim 16, further comprising calculating a plurality of blood pressures of the plurality of second locations on the body of the subject.

19. The method of claim 14, further comprising receiving a set of calibration values, and the calculating the blood pressure comprising using the set of calibration values.

20. The method of claim 14, wherein the first feature of the first signal corresponds to a first time point; and the identifying, for each of the plurality of second signals, the second feature comprises:

selecting a segment of each of the second signals, the segment occurring within a time window from the first time point; and locating the second feature corresponding to a second time point in the segment.

* * * * *